(12) United States Patent
Mata et al.

(10) Patent No.: US 11,559,359 B2
(45) Date of Patent: Jan. 24, 2023

(54) SURGICAL INSTRUMENT MOUNTED DISPLAY SYSTEM

(71) Applicant: DEPUY SYNTHES PRODUCTS, INC., Raynham, MA (US)

(72) Inventors: Mario Mata, Paoli, PA (US); André Furrer, Lüterkofen (CH); Glen Pierson, Glenmoore, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 774 days.

(21) Appl. No.: 16/536,773

(22) Filed: Aug. 9, 2019

(65) Prior Publication Data

US 2021/0038178 A1 Feb. 11, 2021

(51) Int. Cl.
*A61B 34/00* (2016.01)
*A61B 6/00* (2006.01)
(Continued)

(52) U.S. Cl.
CPC ............... *A61B 34/25* (2016.02); *A61B 6/12* (2013.01); *A61B 6/547* (2013.01);
(Continued)

(58) Field of Classification Search
CPC ........... A61B 34/25; A61B 6/12; A61B 6/547; A61B 17/1626; A61B 17/1703;
(Continued)

(56) References Cited

U.S. PATENT DOCUMENTS 5,031,203 A 7/1991 Trecha
7,060,075 B2 6/2006 Govari et al.
(Continued)

FOREIGN PATENT DOCUMENTS

WO 2015072924 A1 5/2015
WO 2017062466 A2 4/2017
WO 2017083992 A1 5/2017

OTHER PUBLICATIONS

Viant, W. J., et al. "A computer assisted orthopaedic surgical system for distal locking of intramedullary nails." Proceedings of the Institution of Mechanical Engineers, Part H: Journal of Engineering in Medicine 211.4 (1997): 293-300. (Year: 1997).*
(Continued)

*Primary Examiner* — Sean D Mattson
(74) *Attorney, Agent, or Firm* — BakerHostetler

(57) ABSTRACT

A surgical instrument assembly may include a processor, a surgical instrument configured to operate on an anatomical structure, and a display coupled to the processor and attached to the surgical instrument. The processor can be configured to determine a position of the medical imaging device, from which the medical imaging device can generate an X-ray image that includes holes of an intramedullary nail shown as circles, for instance perfect circles. In an example, the processor identifies the intramedullary nail, so as to determine an intramedullary nail identity, and determines the position of the medical imaging device based on a portion of at least two locking holes of the intramedullary nail and based on the intramedullary nail identity.

20 Claims, 23 Drawing Sheets

(51) Int. Cl.
  *A61B 17/17*     (2006.01)
  *A61B 6/12*      (2006.01)
  *A61B 17/16*     (2006.01)
  *A61B 90/00*     (2016.01)
  *A61B 34/20*     (2016.01)

(52) U.S. Cl.
  CPC ...... *A61B 17/1626* (2013.01); *A61B 17/1703* (2013.01); *A61B 17/1725* (2013.01); *A61B 2034/2048* (2016.02); *A61B 2090/376* (2016.02)

(58) Field of Classification Search
  CPC ........ A61B 17/1725; A61B 2034/2048; A61B 2090/376
  See application file for complete search history.

(56) References Cited

U.S. PATENT DOCUMENTS

| | | |
|---|---|---|
| 8,332,012 B2 | 12/2012 | Kienzle |
| 8,442,621 B2 | 5/2013 | Gorek et al. |
| 8,623,023 B2 * | 1/2014 | Ritchey .............. A61B 17/1707 606/86 R |
| 9,554,812 B2 | 1/2017 | Inkpen et al. |
| 2002/0077541 A1 * | 6/2002 | Kienzle .............. A61B 17/1703 600/427 |
| 2007/0167698 A1 * | 7/2007 | Lloyd ................ A61B 17/1725 600/407 |
| 2007/0274584 A1 | 11/2007 | Leow et al. |
| 2010/0312103 A1 * | 12/2010 | Gorek .................... A61B 34/20 600/425 |
| 2014/0107471 A1 | 4/2014 | Haider et al. |
| 2014/0148808 A1 | 5/2014 | Inkpen et al. |
| 2015/0271384 A1 | 9/2015 | Chueng et al. |
| 2016/0030062 A1 | 2/2016 | Rich |
| 2016/0225192 A1 | 8/2016 | Jones et al. |
| 2020/0390412 A1 * | 12/2020 | Bertram ................. A61B 6/547 |

OTHER PUBLICATIONS

Smith & Nephew Trigen Sureshot Distal Targeting System V2.1 User Manual, pp. 1-40, 2011.

* cited by examiner

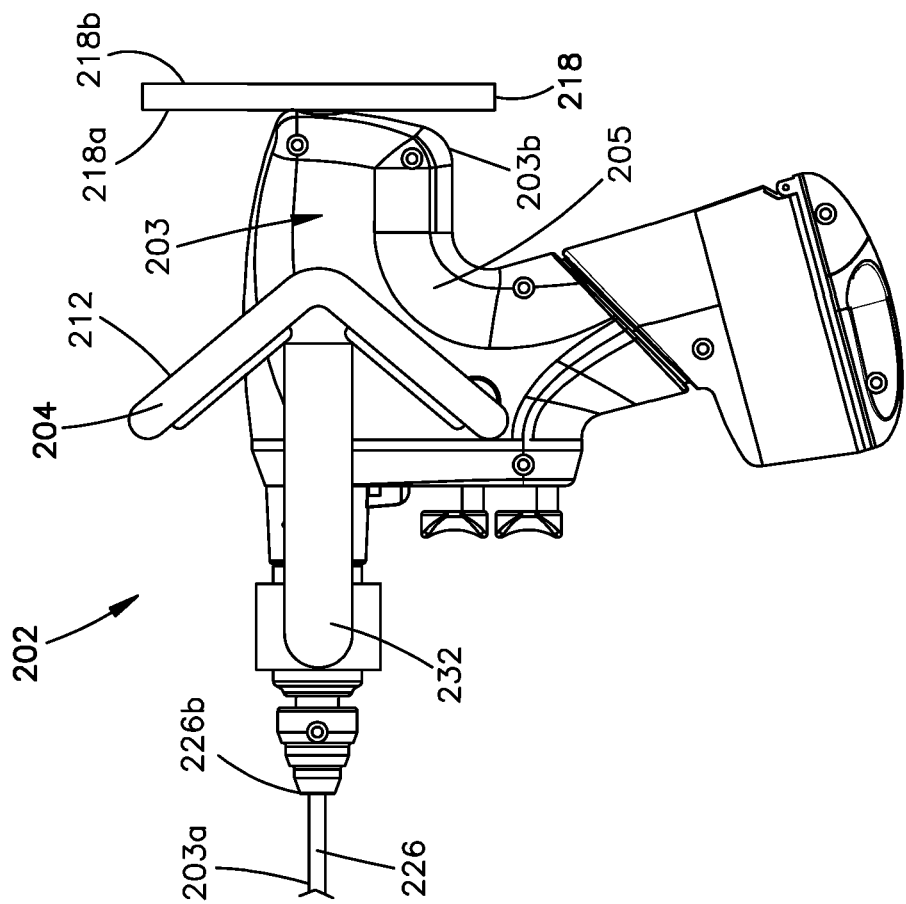
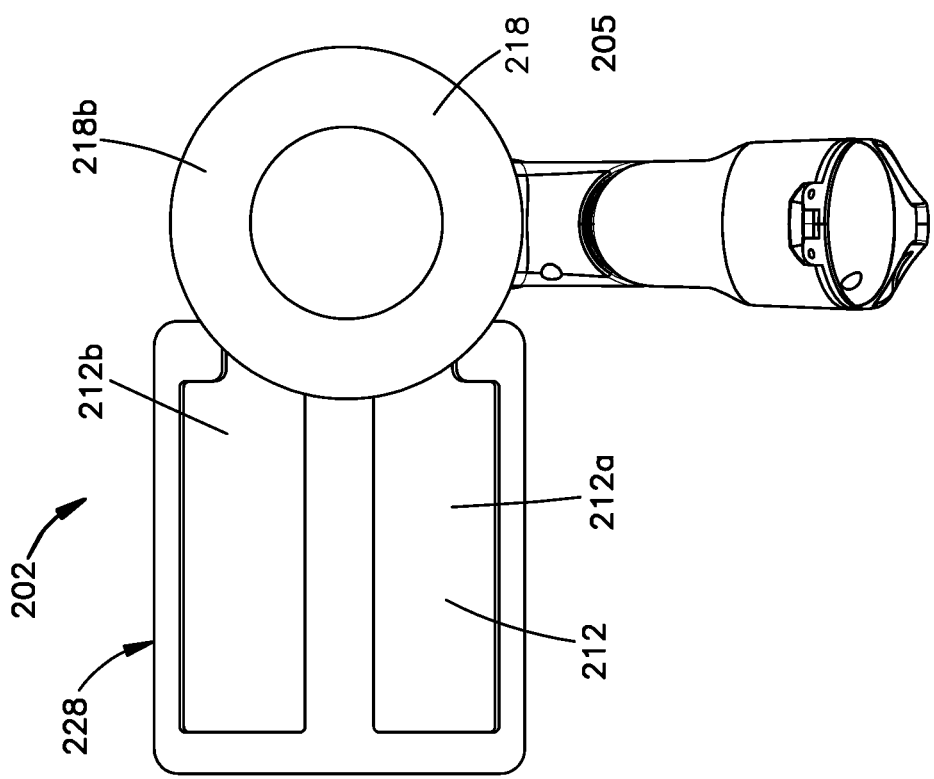

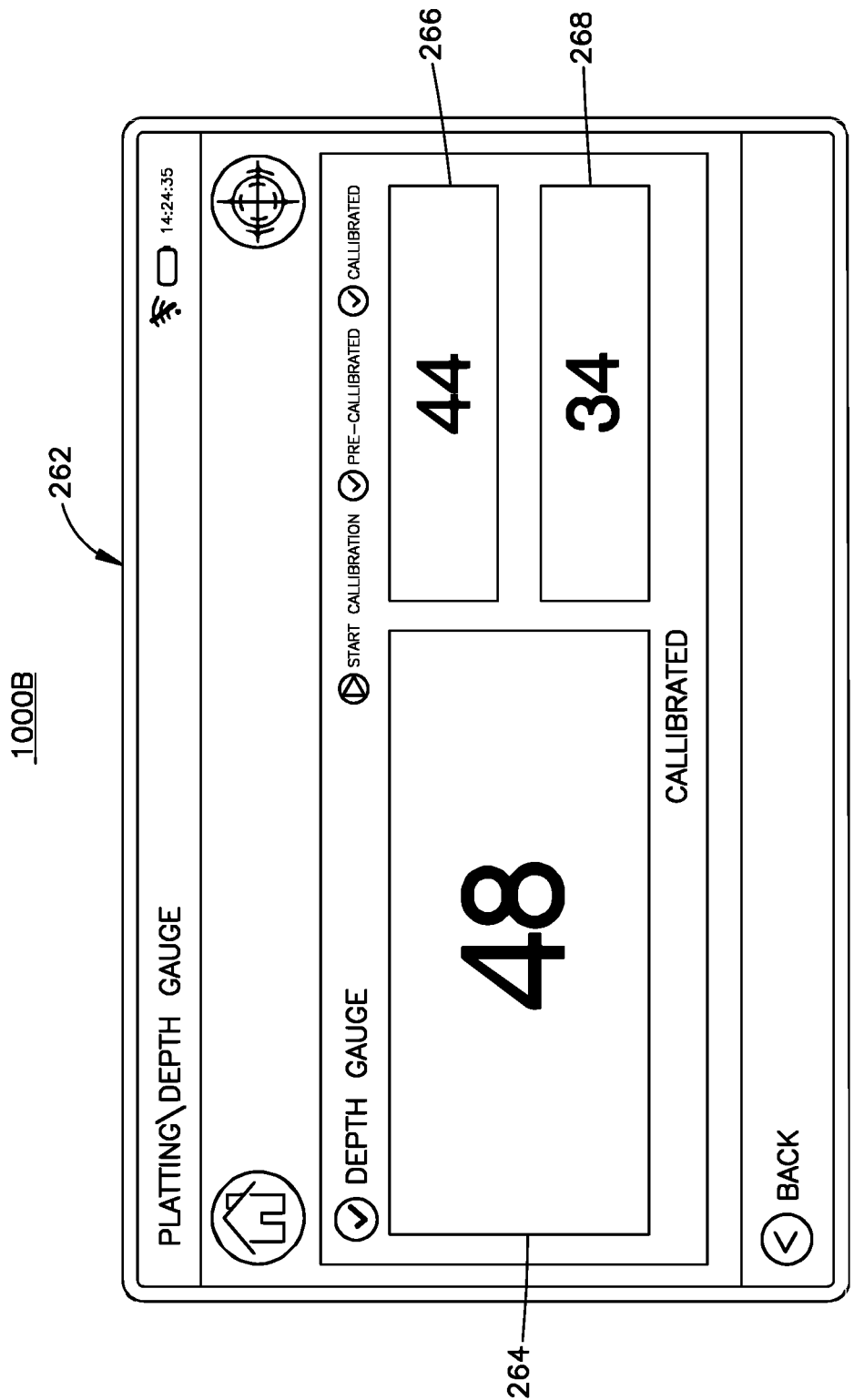

SURGICAL INSTRUMENT MOUNTED DISPLAY SYSTEM

TECHNICAL FIELD

The present invention relates to systems that can be used in conjunction with medical imaging.

BACKGROUND

A C-arm, or a mobile intensifier device, is one example of a medical imaging device that is based on X-ray technology. The name C-arm is derived from the C-shaped arm used to connect an X-ray source and an X-ray detector with one another. Various medical imaging devices, such as a C-arm device, can perform fluoroscopy, which is a type of medical imaging that shows a continuous X-ray image on a monitor. During a fluoroscopy procedure, the X-ray source or transmitter emits X-rays that penetrate a patient's body. The X-ray detector or image intensifier converts the X-rays that pass through the body into a visible image that is displayed on a monitor of the medical imaging device. Because medical imaging devices such as a C-arm device can display high-resolution X-ray images in real time, a physician can monitor progress at any time during an operation, and thus can take appropriate actions based on the displayed images. Monitoring the images, however, is often challenging during certain procedures, for instance during procedures in which attention must be paid to the patient's anatomy as well as the display of the medical imaging device. Furthermore, adjusting the C-arm relative to a patient to locate a screw hole within an intramurally nail can be difficult and time consuming. Aligning the C-arm by freehand with the axis of the screw hole so that the screw appears as a perfect circle is a common process that can result in unnecessary radiation exposure, costly operating time, and stress, among other issues.

SUMMARY

In an example, a surgical instrument assembly includes a processor, a surgical instrument configured to operate on an anatomical structure, and a display coupled to the processor and attached to the surgical instrument. The display can be configured to display fluoroscopic data, for instance X-ray images or video data, of the anatomical structure. The fluoroscopic data is generated by a medical imaging device. The surgical instrument assembly can further include a memory in communication with the processor. The memory can have stored therein instructions that, upon execution by the processor, cause the surgical instrument assembly to receive in real-time, via a wireless communications channel for example, the fluoroscopic data from the imaging device. Further, the surgical instrument can include a proximal end and a working end opposite the proximal end. The working end can be configured to operate on the anatomical structure, and the display can be positioned so as to provide a line of sight to both the working end and the display from a location proximal of the surgical instrument. Further still, the display can be configured to provide a visual indication of an alignment of a cutting instrument of the surgical instrument with respect to a direction of X-ray travel from an X-ray transmitter of the imaging device to an X-ray receiver of the imaging device.

In another example, the surgical instrument assembly can identify an intramedullary nail from a plurality of intramedullary nails so as to determine an intramedullary nail identity. The intramedullary nail can define a plurality of locking holes sized to receive respective locking screws. The surgical instrument assembly can receive a first X-ray image from the medical imaging device. The first X-ray image is generated by the medical imaging device when the medical imaging device is in a first position, such that the first X-ray image includes a portion of the intramedullary nail. The portion of the intramedullary nail includes a portion of at least two of the plurality of locking holes. Based on the portion of the at least two locking holes and the intramedullary nail identity, the surgical instrument assembly can determine a second position of the medical imaging device that is different than the first position, such that, when the medical imaging device is placed in the second position and generates a second X-ray image from the second position, the second X-ray image includes the at least two locking holes shown as respective circles, for instance perfect circles. In particular, the processor can be configured to determine a position of the medical imaging device, from which the medical imaging device can generate an X-ray image that includes holes of an intramedullary nail shown as circles, for instance perfect circles.

In yet another example, an accelerometer of a surgical instrument assembly is calibrated with a direction of X-ray travel from an X-ray generator to an X-ray receiver of a medical imaging device. The surgical instrument assembly can include a drill having a drill bit. The surgical instrument assembly can display an X-ray image of an anatomical structure generated by the medical imaging device. The X-ray image can include a target location. A tip of the drill bit can be positioned on the anatomical structure, and the surgical instrument assembly can display a representation of a position of the tip of the drill bit with the target location. The surgical instrument assembly can further display an orientation image that includes a static region and a movable indicator that is representative of an orientation of the drill bit, wherein the drill is oriented with the direction of X-ray travel when the movable indicator has a predetermined spatial relationship to the static region. A hole can be drilled in the anatomical structure while the tip of the drill bit is aligned with the target location, and while the movable indicator has the predetermined spatial relationship to the static region.

The foregoing summarizes only a few aspects of the present disclosure and is not intended to be reflective of the full scope of the present disclosure. Additional features and advantages of the disclosure are set forth in the following description, may be apparent from the description, or may be learned by practicing the invention. Moreover, both the foregoing summary and following detailed description are exemplary and explanatory and are intended to provide further explanation of the disclosure.

BRIEF DESCRIPTION OF THE DRAWINGS

The foregoing summary, as well as the following detailed description of example embodiments of the present disclosure, will be better understood when read in conjunction with the appended drawings. For the purposes of illustrating the example embodiments of the present disclosure, references to the drawings are made. It should be understood, however, that the application is not limited to the precise arrangements and instrumentalities shown. In the drawings:

FIG. 2C is a rear elevation view of the example surgical instrument assembly.

FIG. 2D is a side elevation view of the example surgical instrument assembly.

FIGS. 10A and 10B are example screen shots of the display of the surgical instrument assembly, showing visual indications of the depth of the tip of the cutting instrument with respect to portions of the anatomical structure.

DETAILED DESCRIPTION

A medical professional can use a medical imaging device, for instance a C-arm device, to perform various medical procedures on a patient. For example, medical professionals can use imaging devices to assess bone fractures, guide surgical procedures, or verify results of surgical repairs. C-arm devices, for example, provide spot imaging and fluoroscopic imaging, which allows the generation of continuous real-time moving images. Such images are provided to a display of the C-arm device. It is recognized herein that, in some cases, the display of the C-arm system is not positioned in a manner that adequately assists a medical professional. In various embodiments described herein, images provided by imaging devices are transmitted in real-time to a display that can be mounted to a surgical instrument, such that fluoroscopic imaging provided by the imaging device can be viewed by a medical professional as the medical professional operates and views a working end of the surgical instrument. The display can receive the images in real-time, such that the images are displayed by the display at the same time that the images are generated by the imaging device. In one example, the display is mounted to a surgical drill, such that fluoroscopic images provided by the imaging device can be viewed during an intramedullary (IM) nailing procedure. In an embodiment, an alignment application can also be rendered by the display mounted to the surgical drill, so as to guide the medical professional during the IM nailing procedure. The display can be interactive and can aid in various aspects of an IM nailing procedure. For example, the display can aid in determining and enabling the proper entry point trajectory of a given IM nail, as well as determining and enabling the proper location and orientation for distal locking screws for the IM nail.

As an initial matter, because fluoroscopy is a type of medical imaging that shows a continuous X-ray image on a monitor, the terms fluoroscopic data, fluoroscopic image, video data, and X-ray image may be used interchangeably herein, without limitation, unless otherwise specified. Thus, an X-ray image may refer to an image generated during a fluoroscopic procedure in which an X-ray beam is passed through the anatomy of a patient. Further, it will be understood that fluoroscopic data can include an X-ray image, video data, or computer-generated visual representations. Thus, fluoroscopic data can include still images or moving images.

Figure 1:
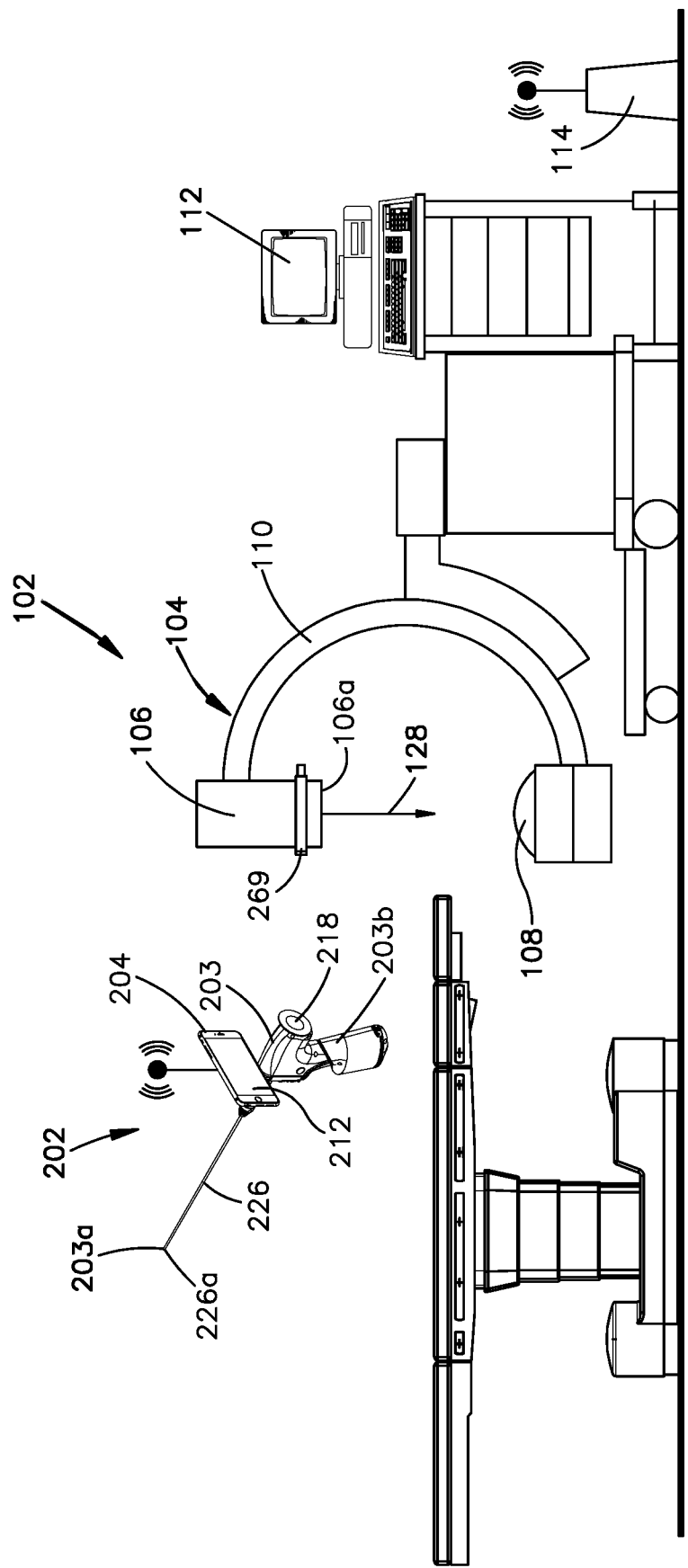
FIG. 1 depicts an example imaging system in accordance with an example embodiment, wherein the example imaging system includes an imaging device in electrical communication with a surgical instrument assembly.

Referring to FIG. 1, a medical imaging system 102 can include a medical imaging device 104 and a surgical instrument assembly 202 in electrical communication with the imaging device 104. The medical imaging device 104, which can be a C-arm device, can include an X-ray generator or transmitter 106 configured to transmit X-rays through a body (e.g., bone) and an X-ray detector or receiver 108 configured to receive the X-rays from the X-ray transmitter 106. Thus, the medical imaging device 104 can define a direction of X-ray travel 128 from the X-ray transmitter 106 to the X-ray receiver 108. The X-ray transmitter 106 can define a flat surface 106a that faces the X-ray receiver 108. The medical imaging device 104 can further include an arm 110 that physically connects the X-ray transmitter 106 with the X-ray receiver 108. The medical imaging device 104 can include a motion sensor 269 configured to detect a position of the medical imaging device 104. The motion sensor 269 can be positioned, for instance on the transmitter 106, and thus on the medical imaging device 104, so as to be configured to detect an orientation of the direction of X-ray travel 128. As described above, the medical imaging device 104 can be configured as a C-arm. Thus, the motion sensor 269 can be mounted onto or otherwise supported by the C-arm. In one example, the motion sensor 269 can be configured as an inertial measurement unit (IMU). In particular, for example, the motion sensor 269 can be configured to detect the position of the transmitter 106, and thus can determine the direction of X-ray travel 128 based on the position of the transmitter 106. The medical imaging device 104 can further be in communication with a medical imaging device display 112 that is configured to display X-ray images from the X-ray detector 108. In some cases, the medical imaging device display 112 can be hard-wired with the X-ray detector 108, such that the display 112 can be in a fixed position relative to the arm 110.

The medical imaging device 104 is presented as a C-arm device to facilitate description of the disclosed subject matter, and is not intended to limit the scope of this disclosure. Further, the imaging system 102 and the imaging device 104 are presented as a medical imaging system and a medical imaging device, respectively, to facilitate description of the disclosed subject matter, and are not intended to limit the scope of this disclosure. Thus, it will be appreciated that other devices, systems, and configurations may be used to implement the embodiments disclosed herein in addition to, or instead of, a system such as the system 102, and all such embodiments are contemplated as within the scope of the present disclosure. It is recognized herein that the position of the display 112 can create problems for a medical professional. For example, in some cases, the medical professional may need to view images or data rendered by the display 112 while viewing a patient positioned between the X-ray generator 106 and the X-ray detector 108. In an example, a medical professional may face challenges placing distal locking screws during an IM nailing procedure due to insufficient assistive instruments or guidance systems, such as an aiming arm used in placement of proximal screws.

Distal screws are commonly inserted in a freehand technique under fluoroscopic guidance. The freehand technique is commonly referred to as the perfect circle technique. Using the freehand technique, an X-ray image can be taken of an intramedullary (IM) nail to locate the screw holes within the nail. Continuing with the example, the C-arm and/or patient (and thus intramedullary nail) can be adjusted and another X-ray image can be taken. The C-arm and/or patient can continue to be adjusted and X-ray images can continue to be generated until the direction of X-ray travel 128 is perpendicular to the screw hole of interest, such that the screw hole of interest appears as a perfect circle on the X-ray image. When the screw hole appears as a circle, the surgeon can determine the appropriate drilling orientation for the screw. It will be understood that this approach, which can be referred to as a trial and error approach, can lack precision and can be costly in terms of time and amount of imaging, thereby resulting in unnecessary radiation exposure to the patient, among other technical drawbacks.

Further, once a perfect circle is established during an IM nailing procedure, it may be difficult to properly align a drill bit to the axis of the distal locking hole due to lack of visibility while using radiographic images. Improper alignment can lead to breaching or cracking of an implant during the drilling of a pilot hole, which can result in implant breakage, poor reduction/fixation, delay of surgery, or the like. It is further recognized herein that an orientation of an X-ray image rendered by the display 112 might not match the orientation of the patient's anatomy, thereby creating further challenges for a medical professional.

As another example of a technical problem addressed by embodiments described herein, before the distal locking screws are placed, a medical professional may face challenges placing the IM nail due to insufficient assistive instruments or guidance systems. IM nails are commonly inserted in a freehand technique under fluoroscopic guidance. Improper placement, however, may result in pain to the patient. For example, different bones and different IM nails require the IM nails to be inserted into the bone at different points of entry and different trajectories, so as to minimize pain. Further, current approaches to determining the appropriate point of entry and trajectory for a specific bone, for instance by consulting a technique guide, can result in errors or delays. In various examples described herein, a surgical instrument assembly can be configured so as guide and help a medical professional during various operations, such as an IM nailing procedure.

Figure 21:
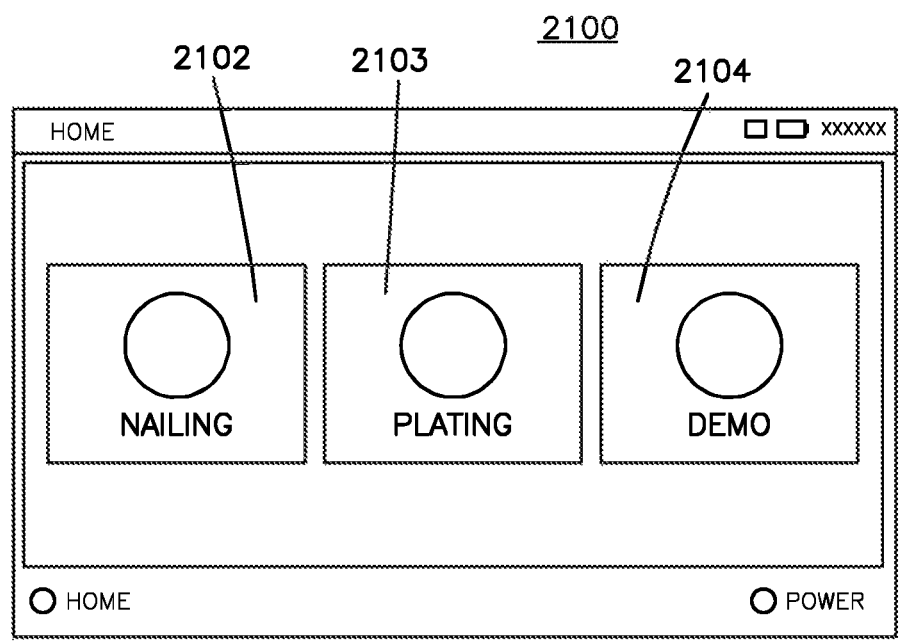
FIG. 21 is another example screen shot of the display of the surgical instrument assembly, wherein the screen shot includes options for performing different operations.

Referring to FIG. 21, a user can select one or more operations by actuating an option on an example user interface 2100, which can be displayed by the display 112. For example, the user can select an IM trajectory option 2104 to perform IM drilling operations. The user can select a plating option 2103 to perform operations associated with securing a plate to a bone. The user can select a nailing option 2102 to perform operations associated with securing a nail with a distal locking screw. It will be understood that alternative or additional options may be rendered by the user interface 2100 as desired. Further, it will be understood that the actuation of the options may result in further displays being rendered, so as to guide the user through a particular operation or phase of an operation.

Figure 3:
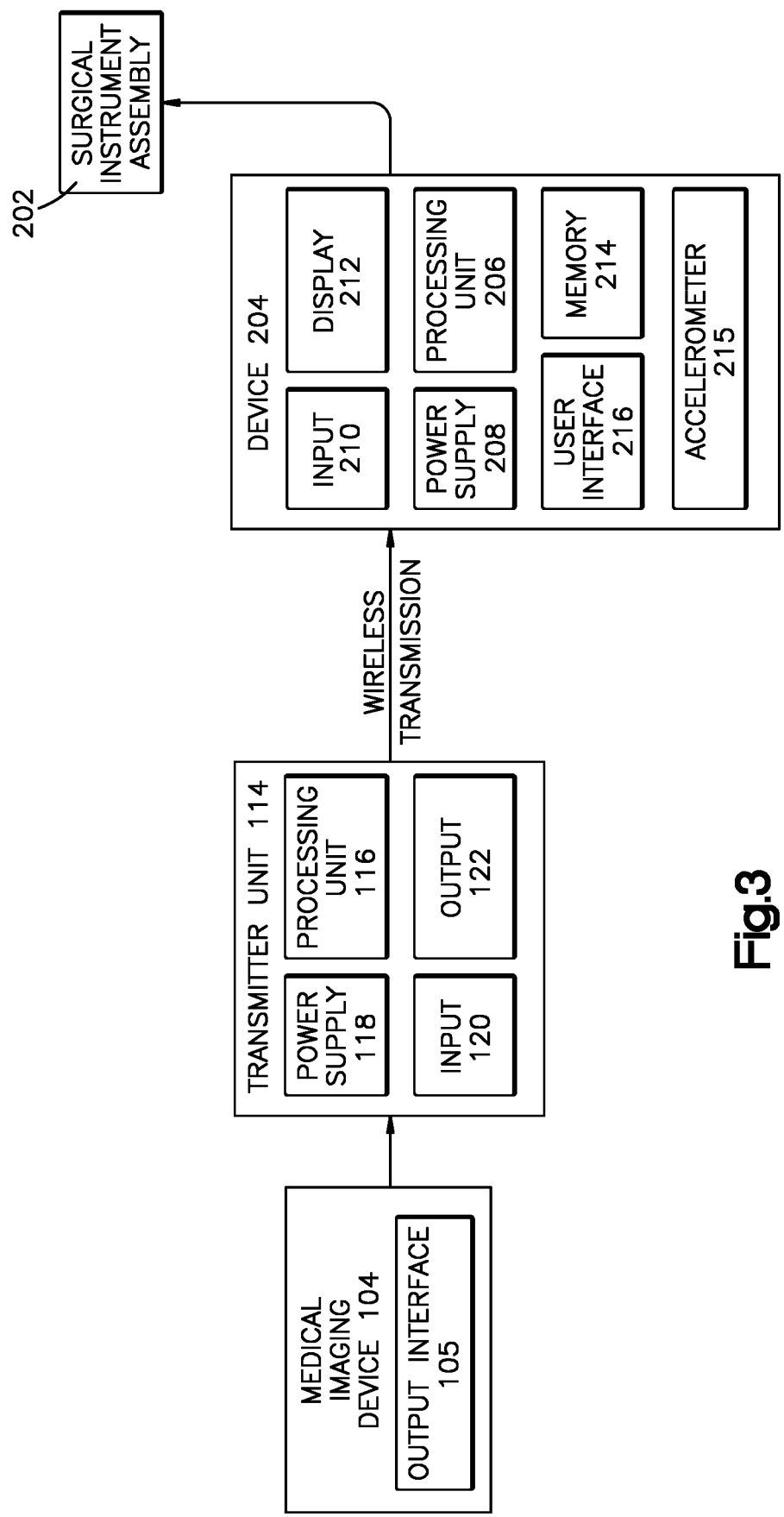
FIG. 3 is a block diagram of example computing devices for use in the imaging system shown in FIG. 1.

Referring now to FIG. 3, in one embodiment, data (e.g., video or still images) provided by the medical imaging device 104 can be received by an instrument application, for instance a fluoroscopic mirror application, which can be a program, such as a software or hardware or combination of both, that can be run on any suitable computing device. A user can use the instrument application to view images generated by the medical imaging device 104. The instrument application can receive and display fluoroscopic images at various locations, for instance at a location that is aligned with the view of a patient.

Figure 2B:
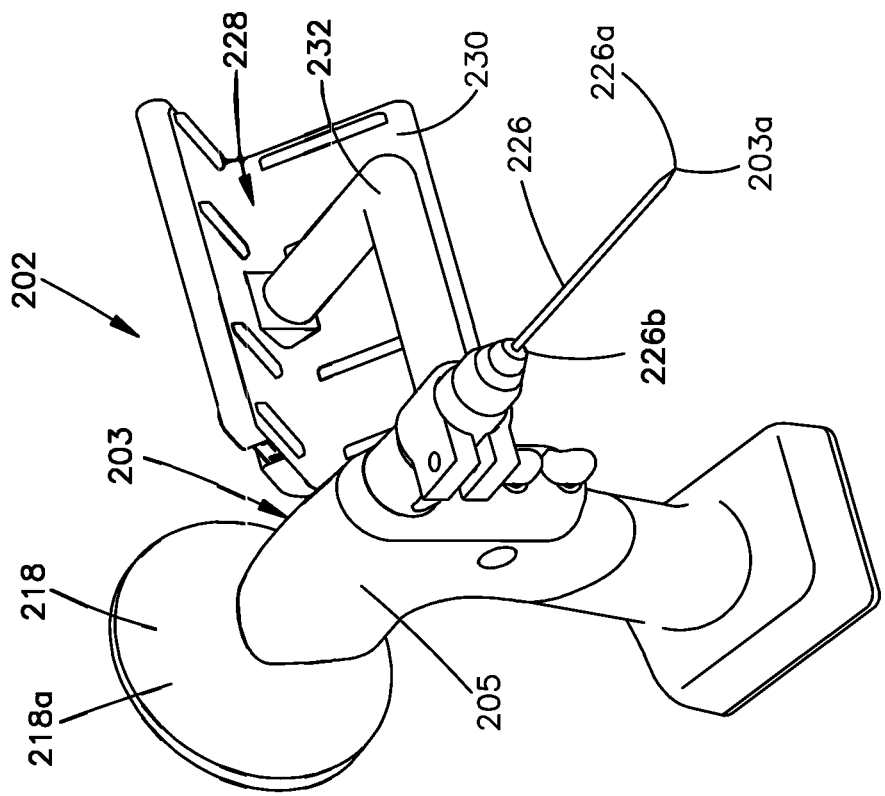
FIGS. 2A and 2B are perspectives view of the example surgical instrument assembly depicted in FIG. 1, which includes a display attached to a surgical instrument.
Figure 2A:
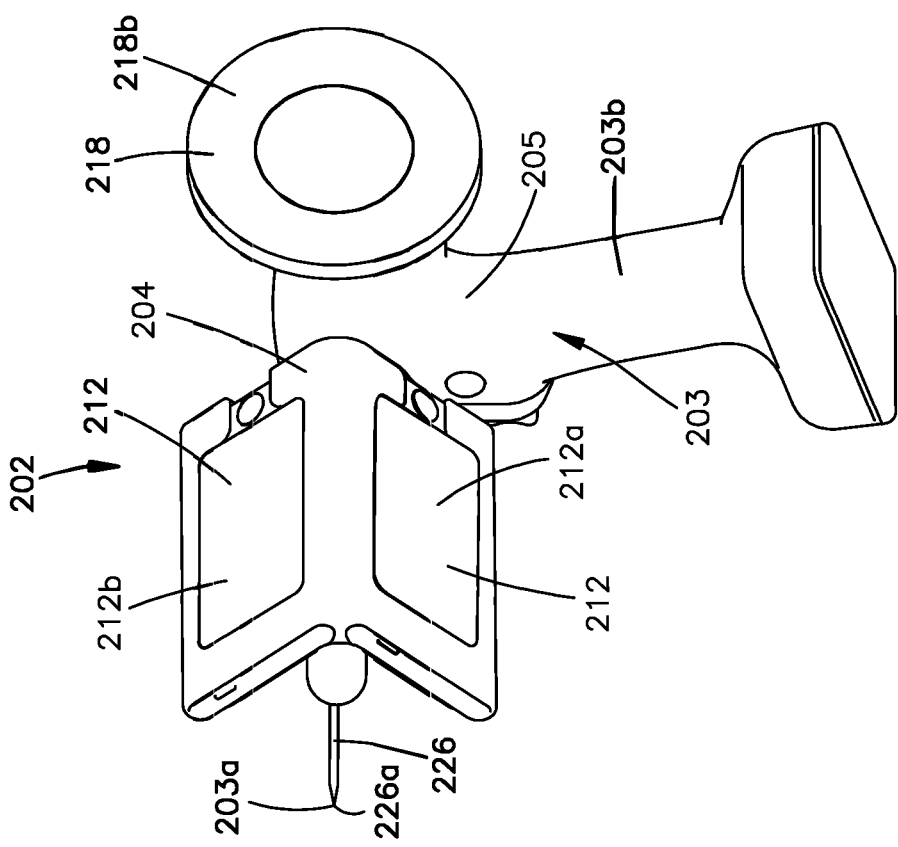

Referring to FIGS. 2 and 3, any suitable computing device 204 can be configured to host the instrument application. It will be understood that the computing device 204 can include any appropriate device, examples of which include a portable computing device, such as a laptop, tablet, or smart phone. In another example, the computing device 204 can be internal to the surgical instrument 203.

In an example configuration, the computing device 204 includes a processing portion or unit 206, a power supply 208, an input portion 210, a display 212, a memory portion 214, a user interface portion 216, and an accelerometer 215. It is emphasized that the block diagram depiction of computing device 204 is an example and not intended to imply a specific implementation and/or configuration. The processing portion 206, input portion 210, display 212, memory 214, user interface 216, and accelerometer 215 can be coupled together to allow communications therebetween. The accelerometer 215 can be configured to generate accelerometer information that corresponds to an orientation of the computing device 204. As should be appreciated, any of the above components may be distributed across one or more separate devices and/or locations.

In various embodiments, the input portion 210 includes a receiver of the computing device 204, a transmitter of the computing device 204, or a combination thereof. The input portion 210 is capable of receiving information, for instance fluoroscopic data in real-time, from the medical imaging device 104. In some cases, the input portion 210 of the computing device 204 can receive positional data from the motion sensor 269 as the medical imaging device 104 changes position. As should be appreciated, transmit and receive functionality may also be provided by one or more devices external to the computing device 204, and thus the surgical instrument assembly 202.

Depending upon the exact configuration and type of processor, the memory portion 214 can be volatile (such as some types of RAM), non-volatile (such as ROM, flash memory, etc.), or a combination thereof. The computing device 204 can include additional storage (e.g., removable storage and/or non-removable storage) including, but not limited to, tape, flash memory, smart cards, CD-ROM, digital versatile disks (DVD) or other optical storage, magnetic cassettes, magnetic tape, magnetic disk storage or other magnetic storage devices, universal serial bus (USB) compatible memory, or any other medium which can be used to store information and which can be accessed by the computing device 204.

The computing device 204 also can contain the user interface portion 216 allowing a user to communicate with the computing device 204. The user interface 216 can include inputs that provide the ability to control the computing device 204, via, for example, buttons, soft keys, a mouse, voice actuated controls, a touch screen, movement of the computing device 204, visual cues (e.g., moving a hand in front of a camera on the computing device 204), or the like. The user interface portion 216 can provide outputs, including visual information (e.g., via a display), audio information (e.g., via speaker), mechanically (e.g., via a vibrating mechanism), or a combination thereof. In various configurations, the user interface portion 216 can include a display, a touch screen, a keyboard, a mouse, an accelerometer, a motion detector, a speaker, a microphone, a camera, a tilt sensor, or any combination thereof. The user interface portion 216 can further include any suitable device for inputting biometric information, such as, for example, fingerprint information, retinal information, voice information, and/or facial characteristic information. Thus, a computer system such as the computing device 204 can include a processor, a display coupled to the processor, and a memory in communication with the processor. The memory can have stored therein instructions that, upon execution by the processor, cause the computer system to perform operations, such as the operations described herein. The display 212 can be configured to display visual information, such as described with reference to FIGS. 4A-D, FIGS. 5A-C, and FIGS. 10A to 22.

Referring to FIGS. 1 and 3, a transmitter unit 114 can be electrically coupled to, or can be part of, the medical imaging device 104. The transmitter unit 114 can be any suitable computing device configured to receive and send images, for instance video signals including fluoroscopic images. It will be understood that the transmitter unit 114 can include any appropriate device, examples of which include a portable computing device, such as a laptop, tablet, or smart phone.

Referring in particular to FIG. 3, in an example configuration, the transmitter unit 114 can include a processing portion or unit 116, a power supply 118, an input portion 120, and an output portion 122. It is emphasized that the block diagram depiction of transmitter unit 114 is an example and not intended to imply a specific implementation and/or configuration. The processing portion 116, input portion 120, and output portion 122 can be coupled together to allow communications therebetween. As should be appreciated, any of the above components may be distributed across one or more separate devices and/or locations.

In various embodiments, the input portion 120 includes a receiver of the transmitter unit 114, and the output portion 122 includes a transmitter of the transmitter unit 114. The input portion 120 is capable of receiving information, for instance fluoroscopic images or video data, from the medical imaging device 104, in particular an output interface 105 of the medical imaging device 104. The output interface 105 can include a coaxial output, a usb output, a component output, a wireless output, or the like. As should be appreciated, transmit and receive functionality may also be provided by the medical imaging device 104. In an example, the transmitter unit 114 is electrically coupled to the output interface 105 of the medical imaging device 104, so as to establish a wired or wireless electrical connection between the transmitter unit 114 and the display 112. The output interface 105 can include or more video output connectors using the matching input module. In an example, the processing portion 116, which can include or more processors running on an embedded operating system, can detect the presence of a signal, for instance a video signal including fluoroscopic images, from the medical imaging device 104. The processing portion 116 can process the signal as necessary for transmitting to the surgical instrument assembly 202. For example, the processing portion 116 can compress the signal so as to reduce the bandwidth that is used for transmitting the signal.

After the processing portion 116 performs processing on the video signal, as necessary, the video signal that can include fluoroscopic images can be sent by the output portion 122 of the transmitter unit 114 to the input portion 210 of the computing device 204. The output portion 122 of the transmitter unit 114 can be configured to transmit fluoroscopic images in accordance with any communication protocol as desired. For example, the output portion 122 can include a ZigBee module connected to the processing portion 206 via a universal serial bus (USB), such that the output portion 122 can send data wirelessly (via a wireless communications channel) in accordance with any ZigBee protocol. The output portion 122 can send video signals, for instance fluoroscopic images, over Wi-Fi, Bluetooth, broadcast, or any other wireless communication channels as desired.

Accordingly, the input portion 210 of the device 204 can receive data or video signals in real-time, for instance fluoroscopic images or positional data, which are sent via a wireless communication channel from the medical imaging device 104. The input portion 210 can be configured to receive ZigBee messages, Wi-Fi messages, Bluetooth messages, broadcast messages, or messages formatted in accordance with any wireless protocol as desired. In an example, when the input portion 210 of the device 204 receives the fluoroscopic images from the medical imaging device 104, the images can be retrieved and verified by the processing portion 206 of the computing device 204. For example, the processing portion 206 can verify that the received images are from the appropriate medical imaging device. The images can be forwarded to the display 212, for example, when the images are verified. The processing portion 206 can also ensure that valid data is displayed. For example, if there is an interruption to the wireless communication channel or connection between the computing device 204 and the medical imaging device 104, the processing portion 206 can identify the interruption, and send a message to the display 212 so that the interruption is conveyed to a medical professional who views the display 212. In some cases, the processor 206 can cause the surgical instrument assembly 202 to display an indication of error on the display 212 when a quality of the communication link between the imaging device 104 and the surgical instrument assembly 202 is below a predetermined threshold. Thus, a wireless point-to-point communication channel or connection between the transmitter unit 114 and the computing device 204 can be established, and the wireless point-to-point connection can be managed by the input portion 210 and the output portion 122 on the physical layer, and the processing portions 116 and 206 at the application layer.

Referring generally to FIGS. 2A-D, 7A-B, and 13, the medical imaging system 102 can include the surgical instrument assembly 202 that can include the computing device 204 mounted to a surgical instrument 203. The surgical instrument 203 can be configured to operate on an anatomical structure, such as an anatomical structure 124. The surgical instrument 203 can define a body 205, and the computing device 204 can be attached anywhere to the body 205 as desired. In an example, referring to FIGS. 2A-D, the computing device 204, and thus the display 212, can be supported by a mount 228. The mount 228 can include a support surface 230 that supports the computing device 204, and thus the display 212. The mount 228 can further include an arm 232 attached to the support surface 230 and the body 205 of the surgical instrument 203, such that the display 212 is in a fixed position relative to the body 205 of the surgical instrument 203. The arm 232 or the support surface 230 can be configured to rotate, so as to adjust the viewing angle of the display 212. The mount 228 can be positioned such that the display does not interfere with the operation of the surgical instrument 203. It will be understood that the computing device 204 can be alternatively mounted to the surgical instrument 205 as desired.

Figure 7A:
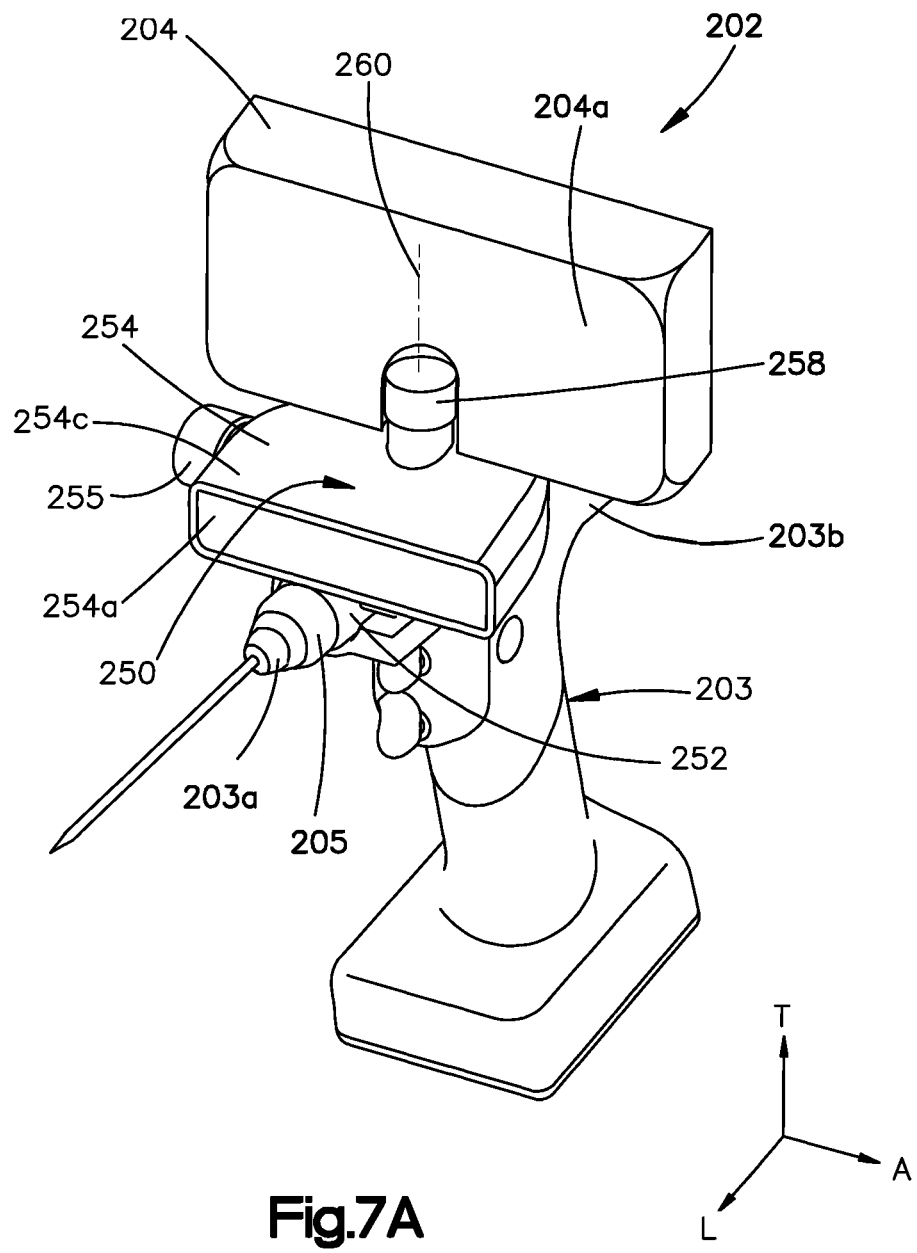
FIGS. 7A and 7B are perspective views of the surgical instrument assembly in accordance with another embodiment, wherein the surgical instrument assembly includes one display and a depth gauge secured to the surgical instrument.
Figure 7B:
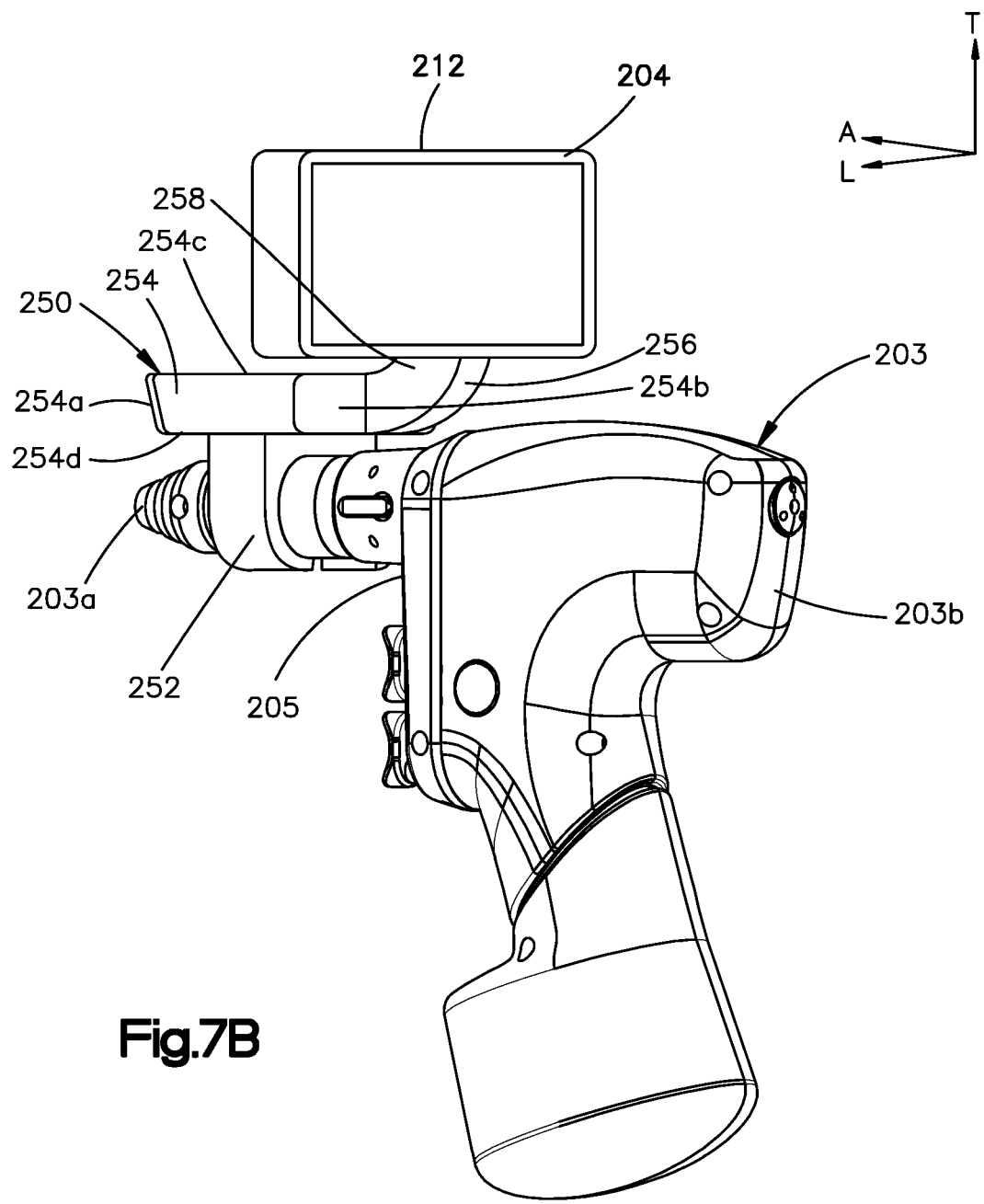
Figure 8:
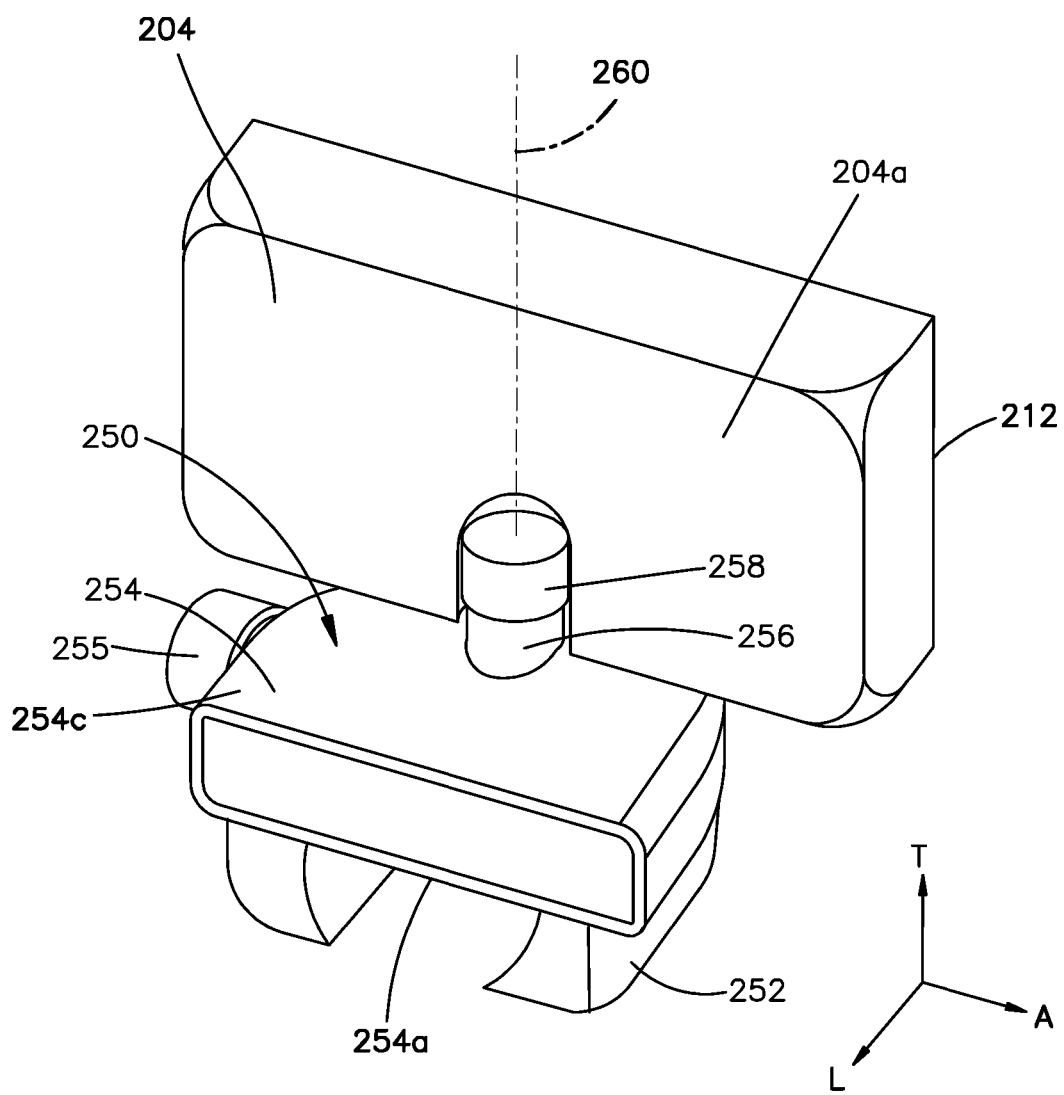
FIG. 8 is a perspective view of the depth gauge and the display shown in FIGS. 7A and 7B.

Referring to FIGS. 7A, 7B, and 8, for example, the surgical instrument assembly 202 can further include a depth gauge 250. The depth gauge 250 can include one or more processors configured to measure, determine, and transmit data related to the depth of a drilling operation performed on an anatomical structure, as further described herein. In some examples, the depth gauge 250 is embodied in accordance with the measuring device suitable for bone screw length determination that is described in International Application Publication No. WO/2017/083992, the disclosure of which is incorporated by reference as if set forth in its entirety herein. It will be understood that the depth gauge 250 can be alternatively embodied. The depth gauge 250 can be in communication with the display 212. The depth gauge 250 can be configured to measure drill depths of the surgical instrument 203 as the surgical instrument 203 operates as a drill. The depth gauge 250 can be secured to the surgical instrument 203 in a fixed position relative to the surgical instrument 203. The depth gauge 250 can be releasably attached or fixed to the body 205 of the surgical instrument 203, so as to be secured in a fixed position relative to the body 205. The depth gauge 250 can be supported by an adaptor 252 that can be secured to the body 205 and the depth gauge 250. The adaptor 252 can be sized as desired to clamp to the body 205, such that the adaptor 252, and thus the depth gauge 250, remain in a fixed position relative to the body 250 as the surgical instrument 203 operates. In an example, the adaptor 252 can be adjusted by moving, for instance turning, an actuator 255. The actuator 255 can be configured as a knob or the like. For instance, the actuator 255 can be turned in a clockwise direction to tighten the adaptor 252, and the actuator can be turned in a counter-clockwise direction to loosen the adaptor 252.

The depth gauge 250 can define a depth gauge body 254 that defines a first or front end 254a and a second or rear end 254b opposite the first end 254a along a longitudinal direction L. The depth gauge body 254 can further define a third or top end 254c and a fourth or bottom end 254d that is opposite the third end 254c along a transverse direction T that is substantially perpendicular to the longitudinal direction L. The adaptor 252 can be secured to the fourth end 254d of the depth gauge 250, though it will be understood that the depth gauge 250 can be alternatively secured to the adaptor 252 as desired. The adaptor 252 can be press fit to the body 205 of the surgical instrument 203. The adaptor 252 can define a clamp collar that is secured to the body 205 of the surgical instrument 203, though it will be understood that the adaptor 252 can be alternatively secured to the surgical instrument 203. In another example, the depth gauge 250 can be secured directly to the surgical instrument 203 without the adaptor 252.

Still referring to FIGS. 7A, 7B, and 8, the depth gauge 250 can further include a depth gauge member 256 that extends from the depth gauge body 254, for instance at the second end 254b of the depth gauge body 254. The computing device 204 can further define a computing device body 204a and a computing device member 258 that extends from the body 204a, so as to attach to the depth gauge member 256. The computing device member 258 can be monolithic or otherwise attached to the computing device body 204a, such that the computing device member 258 can be in a fixed position relative to the computing device body 204a. Further, the display 212 can be in a fixed position relative to the computing device body 204a. Thus, the display 212 can be in a fixed position relative to the computing device member 258. The computing device member 258 can be configured to rotate with respect to the depth gauge member 256. In an example, the computing device member is configured to rotate about an axis 260 that is substantially parallel with the transverse direction T. Thus, the display 212 can be configured to rotate about the axis 260 that is substantially parallel with the transverse direction T. For example, the display 212 can be configured to rotate about the axis 260 so as to adjust the viewing angle of the display 212 while an operation is being performed. The axis 260 can be centered with respect to a width of the display 212 that is defined along a lateral direction A that is substantially perpendicular to both the longitudinal direction L and the transverse direction T. It will be understood that the display 212 can be configured to rotate about alternative axes as desired. The one or more processors of the depth gauge 250 can be communicatively coupled to the computing device 204, and thus to the display 212. In an example, the depth gauge 250 is configured to wirelessly transmit data to the computing device 204. For example, the depth gauge 250 can provide real-time data to the computing device 204 over a Wi-Fi network.

It will also be understood that the computing device 204 can alternatively be monolithic to the surgical instrument 203. Further, though the surgical instrument 203 is depicted as a surgical drill for purposes of example, it will be appreciated that the computing device 204 and the depth gauge 250 can be mounted to, or can be monolithic with, numerous suitable alternative equipment or instruments. For example, the surgical instrument assembly 202 can include an instrument or equipment configured to target an area of bone or other part of the anatomy, remove a medical implant, perform an osteotomy, or any other procedure, for instance any other procedure using fluoroscopy, as desired. Thus, although the anatomical structure 124 is presented as a bone, it will be understood that structures on which the surgical instrument assembly can be configured to operate are not limited to bones.

The computing device 204, and thus the surgical instrument assembly 202, can include the display 212 that can be attached to the surgical instrument. The display 212 can be configured to display fluoroscopic images of the anatomical structure 124 that are generated by the imaging device 104. In an example configuration, the display 212 can display fluoroscopic images of the anatomical structure 124 in real-time, such that the images of the anatomical structure 124 are displayed by the display 212 at the same time that the images are generated by the imaging device 104. In some cases, the display 212, and thus the surgical instrument assembly 202, can include a plurality of displays, for instance a first display 212a and a second display 212b that has a different orientation as compared to an orientation of the first display 212a. In another example configuration, for instance as shown in FIGS. 7A, 7B, 8, and 13, the display 212, and thus the surgical instrument assembly 202, includes only one display.

With reference to FIGS. 2A-D, 7A-B, and 13, the surgical instrument 203 can define a proximal end 203b and a working end 203a opposite the proximal end 203b. The working end 203a can be configured to operate on, for instance cut, drill, or otherwise target, a structure, for instance the anatomical structure 124, of a medical patient. The display 212 can face the proximal end 203b. The display 212, in particular the first display 212a and the second display 212b, can be positioned so as to provide a line of sight to both the working end 203a and the display 212 from a location proximate of the surgical instrument 203. Thus, in some cases, for example, a medical professional can, while operating the surgical instrument 203, view both the display 212 and the working end 203a of the surgical instrument 203.

In an example, the surgical instrument 203 includes a cutting instrument 226 that includes a proximal end 226b adjacent to the body 205 of the surgical instrument 203, and a cutting tip 226a opposite the proximal end 226b of the cutting instrument 226. The cutting tip 226a can define a terminal end of the cutting instrument that is opposite to the proximal end 226b of the cutting instrument 226. The cutting instrument 226 can have the cutting tip 226a that can be configured to remove anatomical material from an anatomical structure, for instance the anatomical structure 124. In the illustrated example, the cutting instrument 226 is a drill bit, and the cutting tip 226a is a tip of the drill bit, though it will be appreciated that other instruments and configurations may be used to implement the embodiments disclosed herein in addition to, or instead of, an instrument such as the cutting instrument 226, and all such embodiments are contemplated as within the scope of the present disclosure.

The surgical instrument assembly 202 can include an alignment tool 218, for instance an axis alignment tool, mounted to the body 205 of the surgical instrument 203. It will be understood that the alignment tool 218 can alternatively be monolithic to the surgical instrument 203. The alignment tool 218 can be rigidly attached to the body 205 of the surgical instrument 203. In an example, the cutting instrument 226 is located at the working end 203a of the surgical instrument 203, and the alignment tool 218 is located at the proximal end 203b of the surgical instrument, though it will be understood that that the alignment tool 218 can be alternatively located as desired. The alignment tool 218 can define a first surface 218a proximate to the surgical instrument 203 and a second surface 218b opposite the first surface 218a. The second surface 218b can define a flat surface, and thus the alignment tool 218 can define a flat surface. Thus, the second surface 218b of the alignment tool 218 can define a plane. The cutting instrument 226 (e.g., drill bit) can be oriented perpendicularly to the plane defined by the second surface 218b of the alignment tool 218. In an example, the alignment tool 218 includes a pin that is oriented perpendicularly to the plane defined by the second surface 218b of the alignment tool. The pin can be configured to be received by a hole defined by the proximal end 203b of the surgical instrument 203. The hole defined by the proximal end 203b of the surgical instrument 203 can have a parallel orientation with the cutting instrument 226, such that, when the pin of the alignment tool 218 is received by the hole defined by the proximal end 203b of the alignment tool 218, the second surface 218b of the alignment tool defines the plane that is perpendicular to the orientation of the cutting instrument 226.

Referring also to FIGS. 4A-D, fluoroscopic images of the anatomical structure 124 can include one or more target locations 126. The target locations 126 can represent locations on the anatomical structure 124 that the surgical instrument 203 can drill, cut, or otherwise target. In accordance with the illustrated example, the target locations 126 can be defined by an implant 125, for instance an IM nail or rod, in a bone. It will be understood that an example operation performed by the surgical instrument assembly is presented as an IM nailing operation to facilitate description of the disclosed subject matter, and the example IM operation is not intended to limit the scope of this disclosure. Thus, it will be appreciated that the surgical instrument assembly 202 may be used to perform other operations in addition to, or instead of, an operation such as the example IM nailing operation, and all such embodiments are contemplated as within the scope of the present disclosure.

Figure 4A:
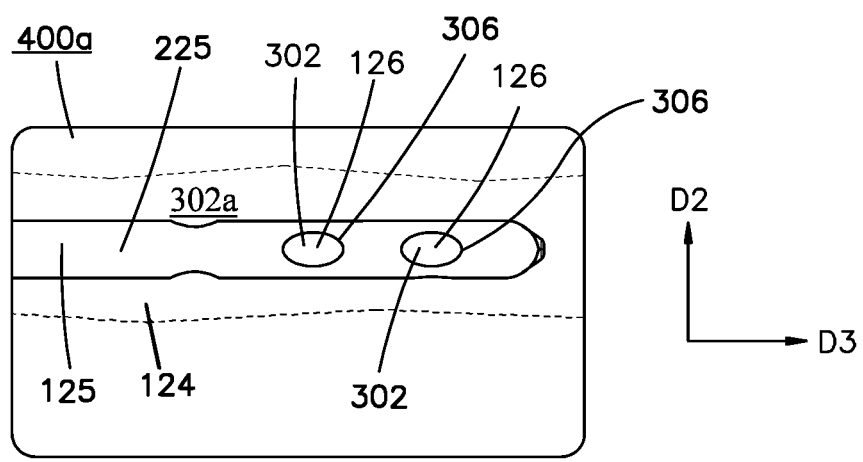
FIG. 4A depicts an example X-ray image of an anatomical structure that can be displayed by the surgical instrument assembly depicted in FIGS. 2A-D, wherein the X-ray image is generated from a first perspective so that the X-ray image includes target locations that appear as ellipses.
Figure 4B:
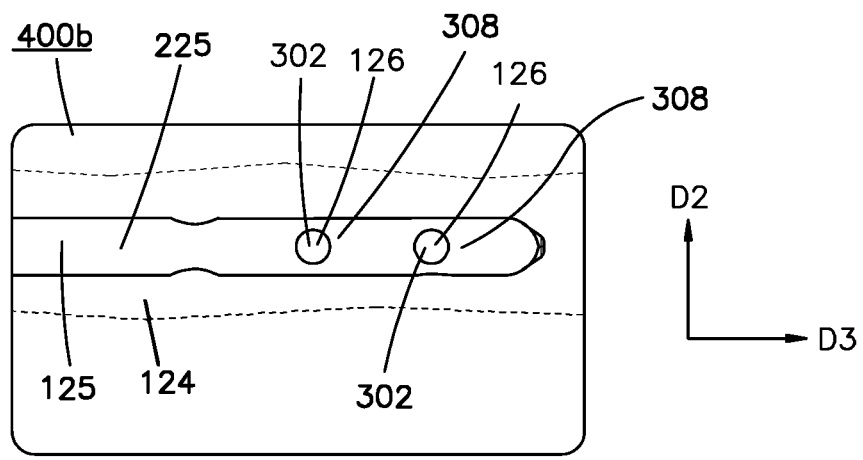
FIG. 4B depicts another example X-ray image of the anatomical structure, wherein the X-ray image is taken from a second perspective so that the target locations appear as perfect circles.

The display 212 can display fluoroscopic images associated with IM nailing operations, among others. The display 212 can display information related to drilling distal locking holes or placing an IM nail within a bone. Further, the display 212 can display images or data associated with the depth gauge 250. Further still, the display 212 can display images or data associated with the depth gauge 250 and/or information related to IM nailing operations at the same time that the display 212 renders fluoroscopic images. The display 212 can be configured to display fluoroscopic images, for instance example fluoroscopic images 400a-d of the anatomical structure 124, generated by, and received from, the medical imaging device 104. Referring in particular to FIG. 4A, the display 212, for instance the first display 212a, can display a first X-ray image 400a, of the implant 125 in the anatomical structure 124. The implant 125 can define one or more target locations 126 at which material can be removed from the anatomical structure 124. In an example IM nailing operation, by viewing the display 212 that displays fluoroscopic images from the imaging device 104, a medical professional can maneuver the patient or the imaging device 104 while viewing the patient and display 212 simultaneously, until the target locations 126 define perfect circles, as illustrated in FIG. 4B. In the IM nailing example, when the one or more target locations 126 define perfect circles, holes can be drilled at the target locations 126 for locking screws.

As used herein in the IM locking hole context, perfect circles and circles can be used interchangeably, unless otherwise specified. A perfect circle or circle can refer to a visual depiction of a locking hole that is within a predetermined threshold as compared to a geometric circle. The predetermined threshold can be defined by an operational tolerance necessary for drilling a hole at the location represented by the circle. In an example, a visual depiction of a locking hole defines a perfect circle when the minimum distance from its center to its perimeter is at least 90% up to 100% of its maximum distance from its center to its perimeter.

Referring again to FIG. 4A, in an example embodiment, perfect circles for distal locking screws can be generated based on the first X-ray image 400a. The first X-ray image 400a can be generated by the medical imaging device 104, and the X-ray image 400a can be received by the processor of the surgical instrument assembly 202. The X-ray image 400a can be generated by the medical imaging device 104 when the medical imaging device 104 is in a first position, such that the X-ray image 400a includes a portion of an implant 125, for instance an IM nail 225. In particular, the portion of the IM nail 225 can be within the direction of X-ray travel 128, such that the X-ray image 400a generated by the medical imaging device 104 in the first position includes the portion of the IM nail 225.

Figure 23C:
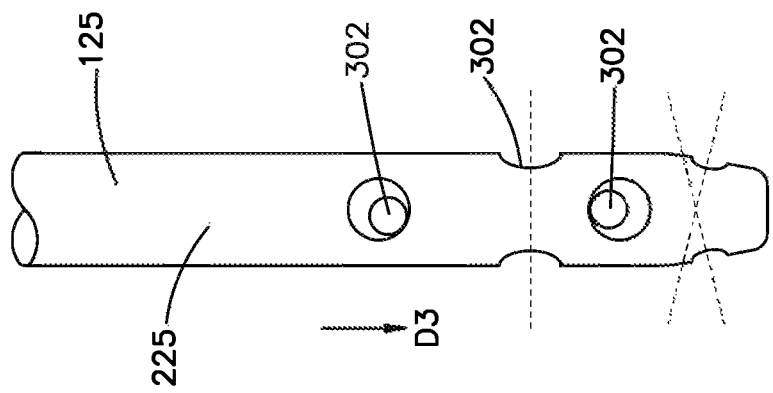
FIG. 23C is another perspective view of the intramedullary nail shown in FIG. 23A.
Figure 23B:
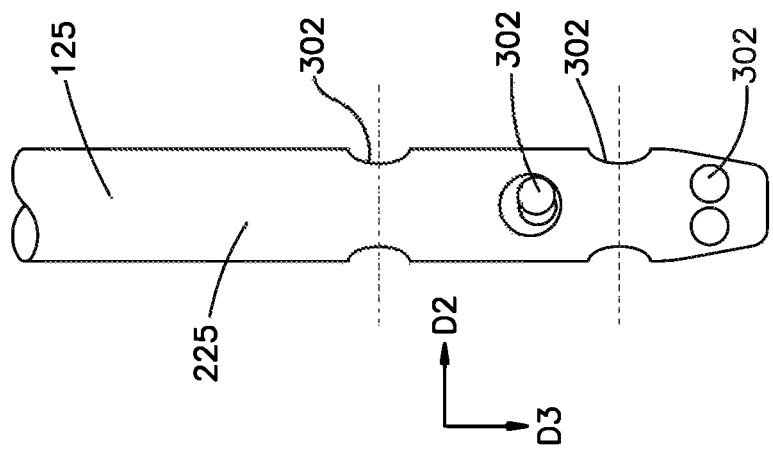
FIG. 23B shows is a perspective view of the intramedullary nail of FIG. 23, shown without the bone and bone screws.
Figure 23A:
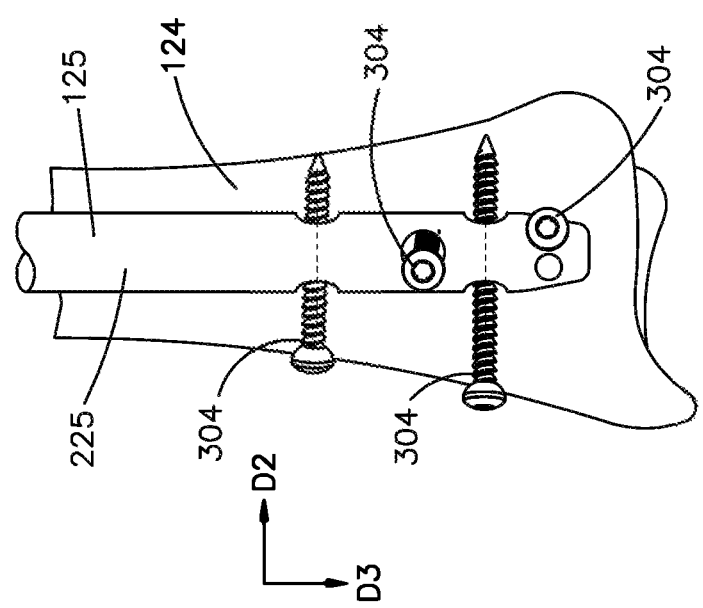
FIG. 23A is a perspective view of an example bone with an intramedullary nail affixed to the bone with bone screws.

Referring also to FIGS. 23A-C, the IM nail 225 can define a plurality of locking holes 302 sized to receive respective locking screws 304, so as to affix or secure the IM nail 225 to the anatomical structure 124. The portion of the IM nail 225 shown in the first X-ray image 400a can include a portion of a locking hole 302, for instance a portion of at least two of the plurality of locking holes 302. The direction of X-ray travel 128 can define a first direction or perspective from which the X-ray image 400a is taken. The IM nail 225 can define a width along a second direction D2, and a length along a third direction D3 that is substantially perpendicular to the second direction D2. The locking holes 302 that appear in the first X-ray image 400a can be spaced apart from each other along the length of the IM nail 225. When the medical imaging device 104 is in the first position from which it generates the first X-ray image 400a, the direction of X-ray travel 128 can be non-orthogonal as compared to at least one, for instance both, of the second and third directions D2 and D3, such that the portion of the at least two locking holes 302 are viewable on the X-ray image 400a as respective ellipses or lenses 306. It will be understood that a lens can define two semicircular defined at their endpoints.

Thus, in operation, the medical imaging device 104 can be caused to be in the first position relative to the IM nail 225. While the medical imaging device 104 is in the first position, the medical imaging device 104 can generate the first X-ray image 400a that includes a portion of the IM nail 225. The portion of the IM nail 225 shown on the first X-ray image 400a can include, and thus the first X-ray image 400a can include, a first visual perspective of a locking hole defined by the IM nail 225. For instance, the first visual perspective can include at least two locking holes defined by the IM nail 225. The first visual perspective can define ellipses or lenses that correspond to respective perimeters of the locking holes shown in the X-ray image 400a. In an example, the first visual perspective from can include less than 50%, for instance 30%, of each of the respective perimeters of the locking holes shown in the X-ray image 400a.

With continuing reference to FIG. 4A, the processor of the surgical instrument assembly 202 can identify the IM nail 225 from a plurality of IM nails so as to determine an IM nail identity. In an example, referring to FIG. 22, the display 212 can be configured to provide a visual indication, for instance a locking hole screen 2200, which includes nail options 2202. The user can select the IM nail used in a given operation by actuating the corresponding nail option 2202, and thus the processor can determine the IM nail identity that is associated with the selected nail option 2202. Thus, in some cases, the processor can determine the identity of the IM nail 225 responsive to a user selection via the user interface 216. For example, the display 212 can display the nail options 2202, which may include visual images or descriptive text of the plurality of IM nails available for a given IM operation. The user, for instance a medical professional, can actuate the appropriate IM nail option 2202, for instance by touch or the like. Alternatively, the processor can be configured to identify the IM nail 225 by recognizing the image of the IM nail 225 from the first X-ray image 400a. Based on the IM nail identity, the processor can retrieve information associated with the IM nail 225, such as its physical properties or characteristics, which can include location and size of locking holes.

Based on the retrieved information concerning the IM nail 225, and thus based on the identity of the IM nail, the processor can identify the locking holes 304 that are visible on the first X-ray image 400a. By way of example, if the IM nail includes five locking holes, the processor can identify which two of the five locking holes appear on the X-ray image 400a, based on the physical properties of the identified IM nail 225. By way of further example, the processor might identify a distance that a particular locking holes is from a terminal end of the IM nail, from the X-ray image 400a, and can compare the distance to the physical properties of the IM nail that can be retrieved, so as to identify the given locking hole. Alternatively, referring again to FIG. 22, the locking hole screen 2200 can include hole options 2204. In some cases, after the IM nail is identified, the hole options 2204 are displayed that correspond to the holes defined by the identified IM nail. The user can select the locking hole that is the subject of a given drilling operation, or the user can select one or more locking holes that are visible in the X-ray image 400a. Thus, in some cases, the processor can determine the locking hole 302 that defines the target location 126 that will be drilled responsive to a user selection via the user interface 216. For example, the display 212 can display the locking hole options 2204, which may include visual images or descriptive text of the plurality of locking holes defined by a particular IM nail. The user, for instance a medical professional, can actuate the appropriate locking hole option 2202, for instance by touch or the like, so that the medical imaging device 104 can make adjustments in its position to generate an image of the appropriate locking hole that depicts the appropriate locking hole as a circle.

Thus, based on the portion of the at least two locking holes 302 shown in the first X-ray image 400a, and based on the IM nail identity, the processor of the surgical instrument assembly can determine a second position of the medical imaging device 104 that is different than the first position. Stated another way, based on the visual perspective of the locking hole shown in the X-ray image 400a, a second position of the medical imaging device 104 relative to the IM nail 225 can be determined. In particular, the direction of X-ray travel 128 defined by the medical imaging device 104 in the second position can be different than the X-ray travel 128 defined by the medical imaging device 104 in the first position. Referring to FIG. 4B, when the medical imaging device 104 is placed in the second position and generates a second X-ray image 400b from the second position, or while the medical imaging device 104 is in the second position, the second X-ray image 400b can include the locking holes 302 shown as respective circles 308. Thus, the second X-ray image 400b can include a second visual perspective of the locking hole shown in the first X-ray image 400a, and the second visual perspective can define a circle that corresponds to a perimeter of the locking hole. In some cases, the second X-ray image 400b includes a second visual perspective of at least two locking holes shown in the first X-ray image 400a, and the second visual perspective can define circles that correspond to respective perimeters of the at least two locking holes.

The direction of X-ray travel 128 can be substantially perpendicular or orthogonal to the length of the IM nail 225 when the medical imaging device 104 is in the second position. The direction of X-ray travel 128 can be substantially perpendicular to the second and third directions D2 and D3 when the medical imaging device 104 is in the second position, such that the at least two locking holes 302 appear as respective circles on the second X-ray image 400b. Thus, the medical imaging device 104 can be caused to be in the second position such that the medical imaging device defines the direction of X-ray travel 128 that is substantially perpendicular to a plane defined by the perimeter of the circle of the second visual perspective (e.g., X-ray image 400b) of the locking holes.

In some cases, the portion of the IM nail 225 shown in the first X-ray image 400a includes a visible portion of only two locking holes. Furthermore, the portion of the two locking holes shown in the X-ray image can be less than 50%, such as less than 30%, of the two locking holes 302, for instance 30% of the surface area of the two locking holes 302. Thus, by way of an example operation, a medical professional can identify an orientation for drilling locking holes by taking one X-ray image of an IM nail that includes only a portion of two locking holes, and the portion of the two locking holes can be viewable as respective ellipses or lenses on the one X-ray image. Thus, based only on the visual perspective of the two locking holes and the physical characteristics of the IM nail, the second position of the medical imaging device can be determined for representing the two locking holes as perfect circles. Further, based only on physical characteristics of the IM nail and the first X-ray image 400a, the orientation for drilling multiple locking holes 302, for instance all locking holes of the IM nail (and not just the locking holes that appear on the X-ray image 400a) can be determined. Consequently, in some cases, the medical imaging device 104 can be adjusted to display every locking hole 302 of a particular IM nail based only on the first X-ray image 400a and the identity of the IM nail. The position of the perfect circle can be determined based on the image of the ellipse using any suitable method, for instance as described in U.S. Pat. No. 9,687,308 issued Jun. 27, 2017, the disclosure of which is hereby incorporated by reference as if set forth in its entirety herein.

Thus, referring to FIG. 4A, the processor of the surgical instrument assembly 202 can determine a third position of the medical imaging device 104, such that, when the medical imaging device 104 is placed in the third position and generates an X-ray image, for instance a third X-ray image, from the third position, the generated X-ray image includes a given locking hole of the IM nail, for instance a third locking hole 302a, shown as a circle, wherein the third locking hole 302a is different than any of the locking holes 302 shown in the first X-ray image 400a (shown as ellipses or lenses) upon which determination of the third position is based. In particular, based on the visual perspective of at least two locking holes 302 shown in the first X-ray image 400a, and based on the physical characteristics of the IM nail 225, a position of the medical imaging device 104 for representing a given locking hole (e.g., locking hole 302a) as a perfect circle can be determined, wherein the given locking hole is not one of the at least two locking holes. Continuing with the example, while the medical imaging device 104 is in the third position, the medical imaging device 104 can generate a third X-ray image that includes a perspective the third locking hole 302a of the IM nail 225, wherein at least the perimeter of the locking hole 302a, for instance the entire locking hole 302a, is not visible in the first X-ray image 400a. The perspective of the locking hole 302a that is generated from the third position can define a circle that corresponds to a perimeter of the locking hole 302a.

The processor of the surgical instrument assembly 202 can retrieve the physical characteristics of a given IM nail from memory based on the identity of the IM nail. In some examples, the medical imaging device 104 automatically changes position to generate an X-ray image of a particular locking hole shown as a circle, in response to the user selecting the particular locking hole on the hole options 2204.

Referring again to FIG. 22, the processor can determine adjustment coordinates 2206 based on the first and second positions of the medical imaging device 104. The display 212, for instance the locking screen 2200, can display the adjust coordinates 2206. The medical imaging device 104 can rely on data from its motion sensor 269 to adjust its position, in particular to adjust the direction of X-ray travel 128, in accordance with the adjustment coordinates 2206. Alternatively, or additionally, a medical professional can move the medical imaging device 104, while the patient and in particular the IM nail 225 remains in the same position it was in when the first X-ray image 400a was generated, in accordance with the adjustment coordinates 2206. The adjustment coordinates 2206 can indicate how the direction of X-ray travel 128 is adjusted to arrive at the second position or third position from the first position. By way of example, the adjustment coordinates 2206 can include a first coordinate 2208 that indicates how the direction of X-ray travel 128 (and thus the medical imaging device 104) is adjusted along a first plane, and a second coordinate 2210 that indicates how the direction of X-ray travel 128 (and thus the medical imaging device 104) is adjusted along a second plane that is substantially perpendicular to the first plane. As shown, the first and second coordinates 2208 and 2210 are shown in terms of degrees relative to their position when the first X-ray image 400a was generated, though it will be understood that embodiments are not limited to degrees. For example, the motion sensor 269 can detect, and the display 212 can display, positional coordinates that correspond to an actual position of the X-ray transmitter 106 and X-ray receiver 108. The positional coordinates can be received from the medical imaging device 104, for instance by the processor of the surgical instrument assembly 202, as the position of the X-ray transmitter 106 and X-ray receiver 108 changes, such that the positional coordinates that are displayed change as the X-ray transmitter 106 and X-ray receiver 108 move.

Figure 22:
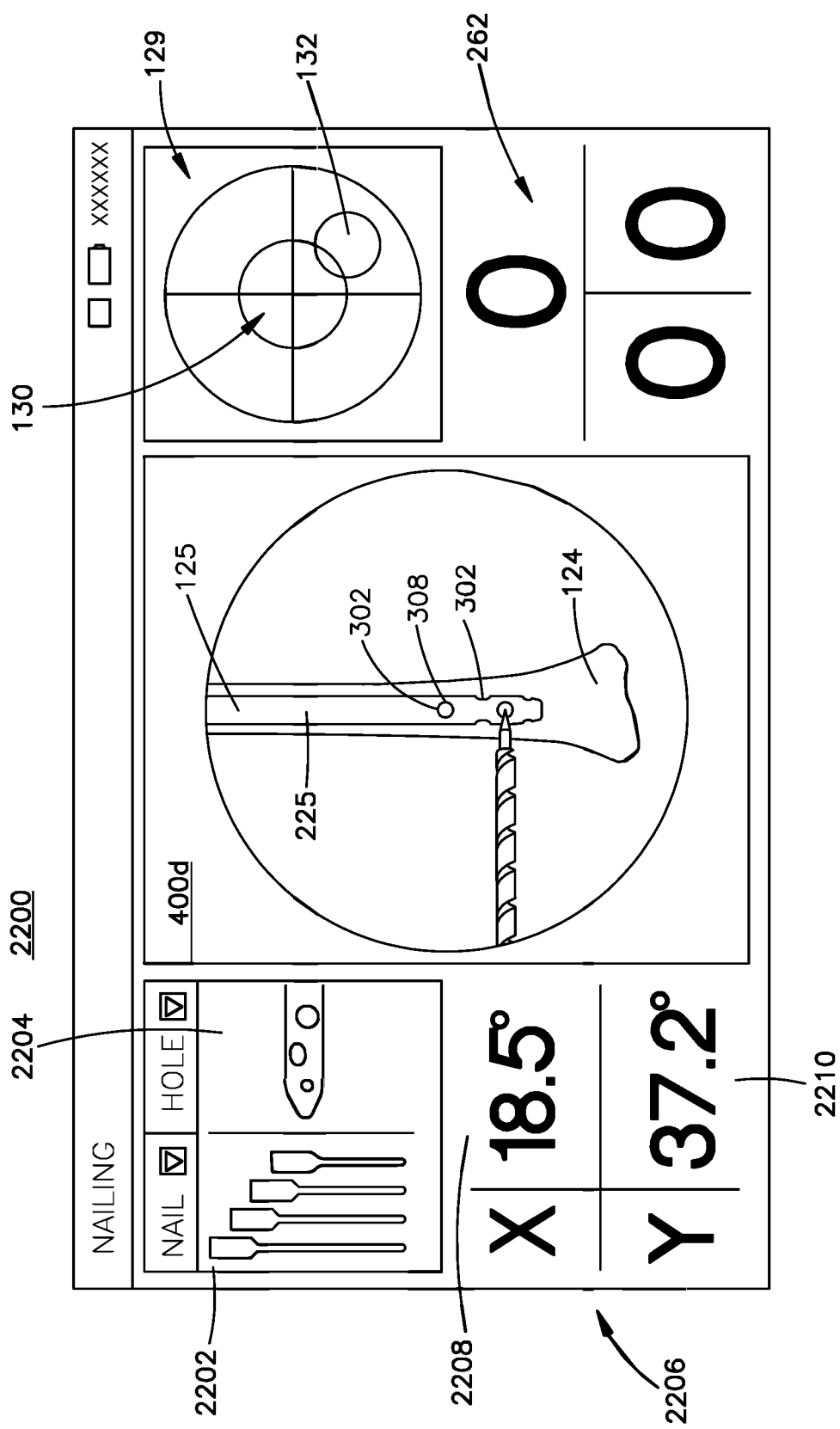
FIG. 22 is another example screenshot of the display of the surgical instrument assembly, showing the example X-ray image from FIG. 4A and example coordinate information that indicate adjustments that can be made to the imaging device so that the target locations for bone screws appear as perfect circles on the X-ray image.

With continuing reference to FIG. 22, the display 212 can be configured to indicate the second position and/or third position of the medical imaging device 104 in response to the processor of the surgical instrument assembly 202 receiving the first X-ray image 400a from the medical imaging device 104. It will be understood that the indication can include adjustment coordinates 2206, or the indication can include audible commands or alternative graphical indications as desired, such that a user can adjust the medical imaging device 104 from the first position to another position so as to generate an image showing locking holes as perfect circles, for instance the second or third positions. In an example operation, when the medical imaging device 104 is in the second position in which a given locking hole is displayed as a perfect circle, a hole is drilled for the given locking hole along the direction of X-ray travel 128 defined by the medical imaging device 104 in the second position.

Figure 4C:
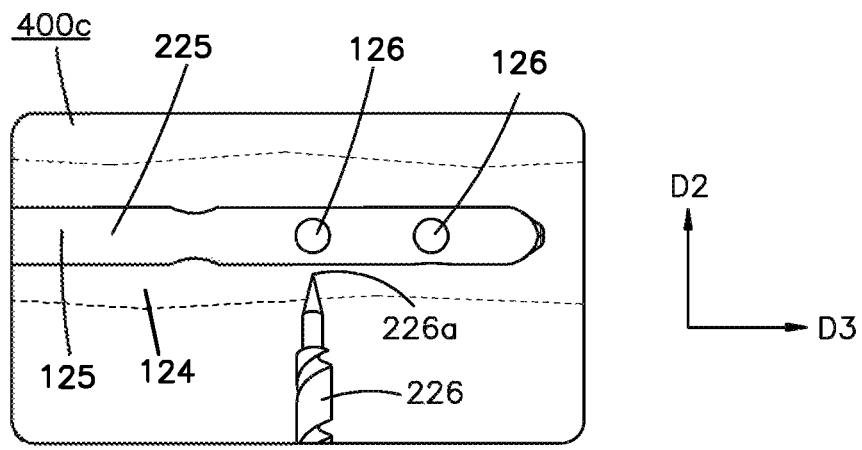
FIG. 4C depicts another example X-ray image of the anatomical structure, showing a position of a cutting instrument of the surgical instrument assembly relative to the target location of the anatomical structure.
Figure 4D:
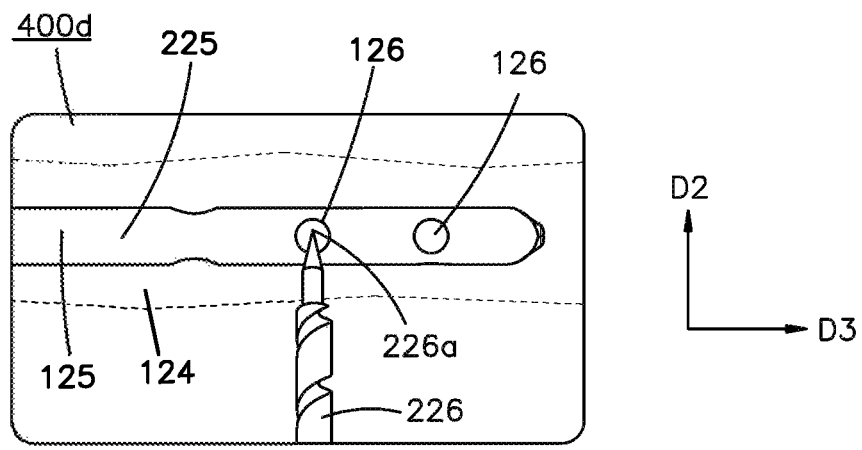
FIG. 4D depicts yet another example X-ray image of the anatomical structure, wherein a tip of the cutting instrument is positioned over the target location.

Referring now to FIG. 4C, the display 212 can display the example fluoroscopic image 400c. Thus, the display 212 can be configured to display a position of the cutting tip 226a of the cutting instrument 226 relative to the target location 126 on the fluoroscopic images of the anatomical structure 124. The fluoroscopic image 400c can depict, for example, the position of the cutting tip 226a that is shown in FIG. 6B. The cutting tip 226a can be configured to remove anatomical material from the one or more target locations 126 of the anatomical structure 124. Further, as shown in FIG. 4D, the tip 226a of the cutting instrument 226 (e.g., drill bit) can be positioned on the anatomical structure 124, for instance at the center of the target location 126. The display 212 can be positioned so as to provide a line of sight to both the tip 226a and the display 212 from a location proximate of the surgical instrument 203, such that a medical professional can view both the fluoroscopic images 400c and 400d, and thus the tip 226a, and the anatomical structure 124, so as to center the tip 226a at the target location 126. The display 212 of the surgical instrument 203 can mirror the display 112 of the medical imaging device 104, such that the display 212 of the surgical instrument assembly 202 can render the same images that the display 112 of the imaging device 104 renders at the same time, so as to display images in real-time.

In some cases, for instance based on a user selection via the user interface 216, the surgical instrument assembly 202 can rotate the displayed fluoroscopic images on the display 212 to a rotated orientation such that a vertical or horizontal direction on the display 212 corresponds with a vertical or horizontal direction, respectively, of movement of the surgical instrument 203 relative to the anatomical structure 124. Thus, in some cases, the fluoroscopic images in the rotated orientation that are displayed by the display 212 can be rotated as compared to the fluoroscopic images displayed on the medical imaging device display 112 that is separate from the display 212 that is coupled to the surgical instrument 203.

Figure 5A:
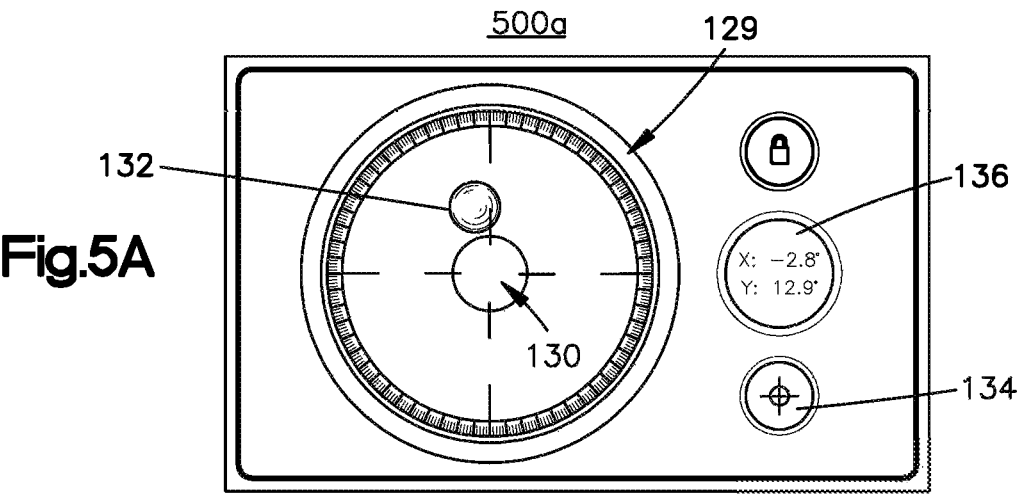
FIG. 5A is an example screen shot of the display of the surgical instrument assembly, showing a visual indication of an alignment of the cutting instrument with respect to a direction of X-ray travel from an X-ray transmitter to an X-ray receiver of the imaging device, wherein the cutting instrument is out of alignment with respect to a first direction.
Figure 5B:
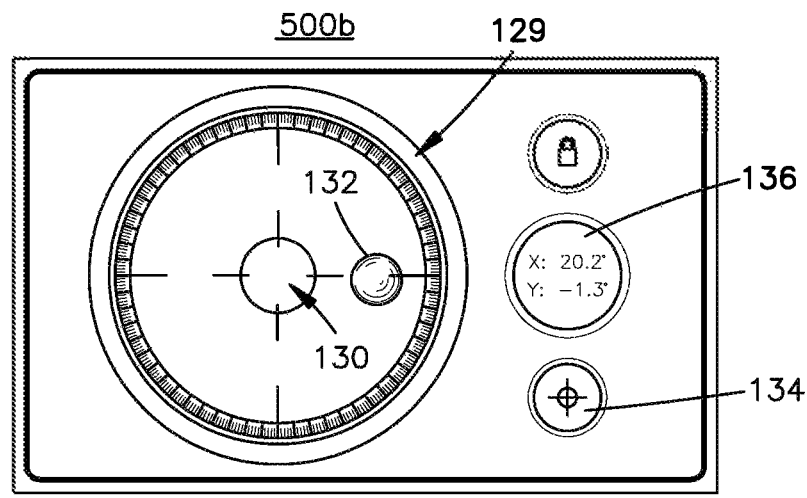
FIG. 5B is another example screen shot of the display of the surgical instrument assembly, showing the visual indication of the alignment of the cutting instrument with respect to the direction of X-ray travel, wherein the cutting instrument is out of alignment with respect to a second direction that is substantially perpendicular to the first direction.
Figure 5C:
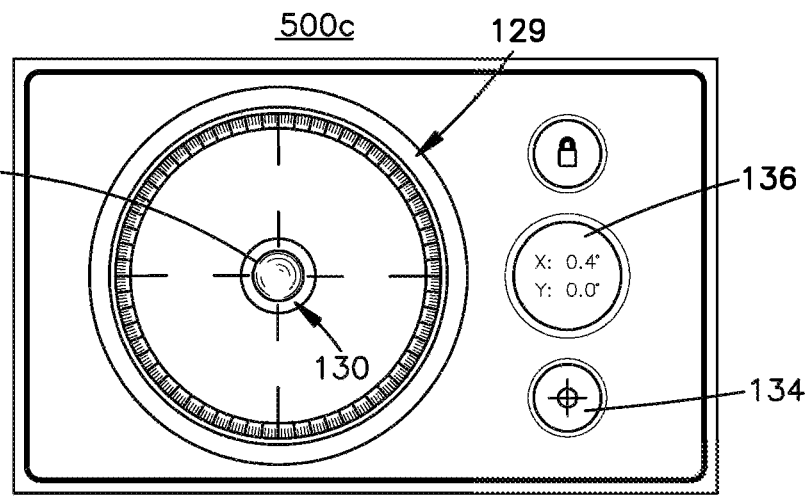
FIG. 5C is another example screen shot of the display of the surgical instrument assembly, showing the visual indication of the alignment of the cutting instrument with respect to the direction of X-ray travel, wherein the cutting instrument is aligned with the direction of X-ray travel such that the cutting instrument and the direction of X-ray travel have the same orientation.

Referring now to FIGS. 5A-C, the display 212 can also be configured to provide a visual indication, for instance an orientation image 129, of an alignment of the cutting tip 226a with respect to the direction of X-ray travel 128 from the X-ray transmitter 106 to the X-ray receiver 108. In an example, the display 212 includes the first display 212a and the second display 212*b*, and the first display 212*a* is configured to display fluoroscopic images (e.g., fluoroscopic images 400*a-c*) from the imaging device 104, and the second display 212*b* is configured to display orientation screens (e.g., orientation screens 500*a-c*) that include a visual indication of an orientation of the cutting instrument 226. It will be understood that the first display 212*a* can also, or alternatively, display orientation screens, and the second display 212*b* can also, or alternatively, display fluoroscopic images. Further, the display 212 can, in some cases, include only one display, which can display both fluoroscopic images and orientation screens at the same time. Further still, referring to FIGS. 11 and 12, the display 212 can, in some cases, include only one display that can display any combination of fluoroscopic images, orientation screens, and depth gauge data at the same time. In an example, a user can select an option via the user interface 216 to select which of the fluoroscopic images, orientation screens, or depth gauge data are displayed by the display 212. In another example, the display 212 can be separated, for instance split in half or split in thirds, such that any combination of the fluoroscopic images, orientation screens, and depth gauge data can be displayed by the display 212 at the same time. It will be understood that the examples described herein of images (e.g., FIGS. 4A-C, 5A-C, 10A-22) that can be displayed by the display 212 are not exhaustive. The display 212 can provide a user with various information via a variety of arrangements or alternative visual depictions.

The visual indication of alignment, for instance the orientation image 129, can be based on the direction of X-ray travel 128, and can further be based on accelerometer information that corresponds to an orientation of the cutting instrument 226. For example, the accelerometer 215 of the surgical instrument assembly 202 can be calibrated with the direction of X-ray travel 128 travel from the X-ray generator 106 to the X-ray receiver 108 of the medical imaging device 104. In an example calibration, the alignment tool 218 that is attached to the surgical instrument 203 is configured to register with a surface of the medical imaging device 104 that has a predetermined orientation so as to align the cutting instrument 226 (e.g., drill bit) with the direction of X-ray travel 128. In one example, the alignment tool 218 is configured to register with the flat surface 106*a* of the X-ray transmitter, though it will be understood that the alignment tool 218 can be configured to register with other surfaces of the medical imaging device 104 as desired. In particular, the second surface 218*b* of the alignment tool 218 can be a flat surface that can abut the flat surface 106*a* of the medical imaging device 104 when the cutting instrument 226 is aligned with the direction of X-ray travel 128. Continuing with the example, a zero value can be set when the surface 218*b* of the alignment tool 218 abuts the flat surface 106*a* of the X-ray generator 106, so as to calibrate the accelerometer 215 with the medical imaging device 104, in particular the direction of X-ray beams generated by the medical imaging device 104. In one example, to set the zero value, thereby calibrating the accelerometer 215 with the direction of X-ray travel 128, a user can actuate a calibration option 134 on the display 212 when the surface 218*b* of the alignment tool is flat against the flat surface 106*a* of the X-ray generator 106, such that the zero value is set when the cutting instrument 226 is oriented along the direction of X-ray travel 128.

In another example, a calibration instrument can be part of, or attached to, the medical imaging device 104. When the medical imaging device 104, and in particular the direction of X-ray travel 128, is oriented in the desired position to perform an operation, the calibration instrument of the medical imaging device 104 can identify a zero value relative to gravity, such that the zero value corresponds to the desired direction of X-ray travel 128. The calibration instrument of the medical imaging device 104 can send the zero value relative to gravity to the accelerometer 215. Thus, the surgical instrument assembly 202 can receive, from the medical imaging device 104, a zero value representative of the direction of X-ray travel 128 from the X-ray generator 106 to the X-ray receiver 108 of the medical imaging device 104, so as to calibrate the accelerometer 215 of the surgical instrument assembly 202 with the direction of X-ray travel 128 defined by the medical imaging device 104. The accelerometer 215 can set its zero value relative to gravity to the zero value that it receives from the calibration instrument of the medical imaging device 104, thereby calibrating the accelerometer 215 with the direction of X-ray travel 128. Thus, the accelerometer 215 can indicate the zero value when the cutting instrument 226 is oriented along the direction of X-ray travel 128.

In an example, the accelerometer 215 corresponds to an orientation of the display 212. Thus, in some cases, when the orientation of the display 212 with respect to the cutting instrument 226 is adjusted, the zero value is re-set to re-calibrate the accelerometer 215 with the direction of X-ray travel 128. In some examples, the display 212 has one or more preconfigured orientations (e.g., 90 degrees, 75 degrees, etc.) with respect to the cutting instrument 226. Thus, in some cases, after calibration at a first preconfigured orientation, the display 212 can be moved to a second preconfigured orientation. In an example, the user can select, using the user interface 216, the preconfigured orientation at which the display 212 is positioned. The accelerometer 215 can receive the second preconfigured orientation, and adjust the zero value accordingly, such that the display 212 is adjusted without the accelerometer being re-calibrated. In yet another example, the medical imaging device 104 includes an accelerometer that can identify a change in orientation of the direction of X-ray travel. In this example, the accelerometer of the medical imaging device can send the change in orientation of the direction of X-ray travel to the surgical instrument assembly 202, such that the zero value can be re-set without re-calibrating the accelerometer 215. Thus, the zero value can be adjusted in accordance with a change in the orientation of the X-ray generator 106 and X-ray receiver 108.

When the accelerometer 215 of the surgical instrument assembly 202 is calibrated with the direction of X-ray travel, for example, the accelerometer can generate accelerometer information that indicates an orientation of the cutting instrument 226 relative to the direction of X-ray travel 128. The accelerometer information can be displayed by the display 212 in various orientation screens, for instance orientation screens 500*a-c*, which can include the orientation image 129. By way of an IM nailing example, by viewing the orientation image 129 while using the surgical instrument assembly 202, the cutting instrument 226 can be maintained at the proper orientation while drilling. That is, holes can be drilled at the target locations 126 that define perfect circles.

For example, referring to FIGS. 5A-5C, the orientation screens 500*a-c* can include the orientation image 129 that can include a static region 130 and a movable indicator 132. The movable indicator 132 can be representative of the orientation of the cutting instrument 226. In an example, the cutting instrument 226 is oriented with the direction of X-ray travel 128 when the movable indicator 132 has a predetermined spatial relationship to the static region 130. In an example, a hole is drilled in the anatomical structure 124 while the tip 226a of the cutting instrument 226 (e.g., drill bit) is aligned with the target location 126, and the movable indicator 132 has the predetermined spatial relationship to the static region 130. It will be understood that the predetermined spatial relationship can vary as desired. In some cases, for example, the cutting instrument 226 is oriented with the direction of X-ray travel 128 when the movable indicator 132 overlies the static region 130. In some cases, as shown in FIG. 5C, the cutting instrument 226 is oriented with the direction of X-ray travel 128 when the movable indicator 132 is within a boundary defined by the static region 130.

Figure 14A:
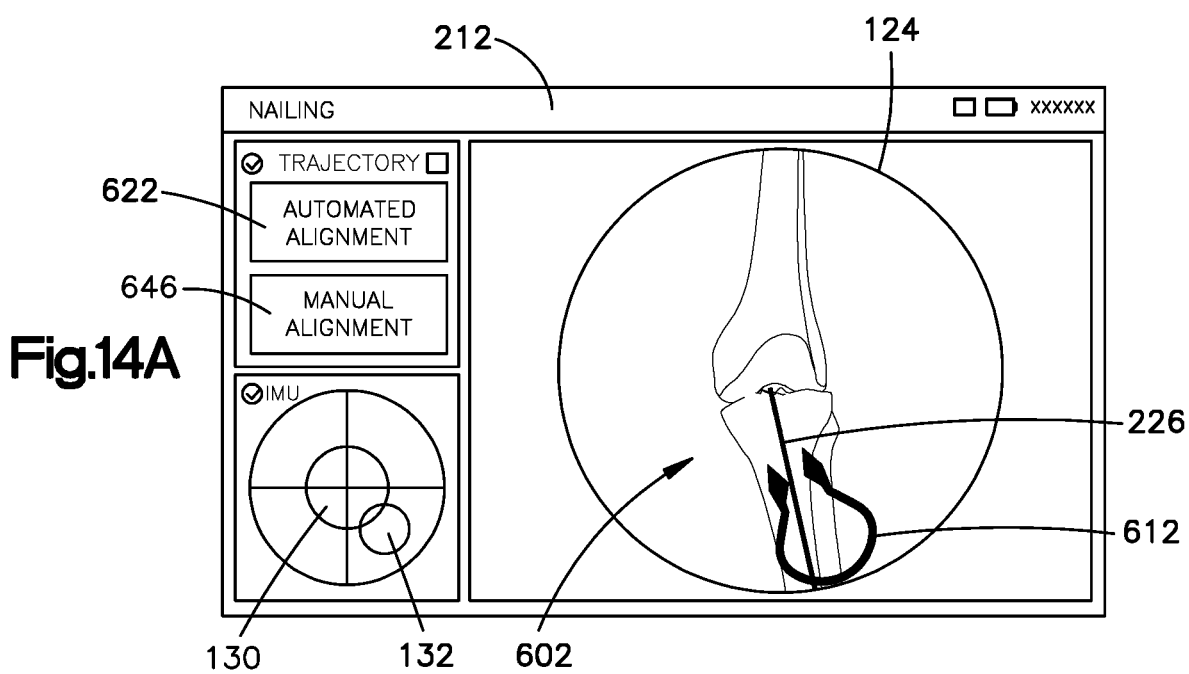
FIG. 14A is an example screen shot of the display of the surgical instrument assembly, showing an X-ray image of an anatomical structure from a first or an anteroposterior (AP) view, wherein the X-ray image includes the cutting instrument positioned to enter the anatomical structure for a specific intramedullary (IM) nailing procedure.

As described above with reference to FIGS. 4A-D, the display 212 can display fluoroscopic images and user interfaces associated with placing locking screws to secure an IM nail. Referring now to FIGS. 13 to 20, the display 212 can additionally, or alternatively, display X-ray or fluoroscopic images and user interfaces associated with placing the implant 125, for instance an IM nail. The display 212 can be configured to display X-ray images, for instance example X-ray data or image 602 (FIGS. 13, 14A, 14B), X-ray image 604 (FIG. 15), X-ray image 606 (FIG. 16), X-ray image 608 (FIG. 17), X-ray image 610 (FIG. 18), and X-ray images 630a and 630b (FIG. 20). As used herein, unless otherwise specified, X-ray data and X-ray image can be used interchangeably, without limitation. Referring in particular to FIG. 14A, the display 212 can display the X-ray data 602 of the anatomical structure 124. In accordance with the illustrated example, the X-ray data 602 includes the cutting instrument 226, which is positioned to drill a hole in the anatomical structure 224 for the implant 125. The X-ray data 602 further includes a clamp 612 positioned to move soft tissue for the drilling operation. In an example, a hole can be drilled so as to meet the IM canal of the anatomical structure or bone 124. Thus, the hole can define a point of entry into the bone and a trajectory between the point of entry and the IM canal, and the implant 125, for instance an IM nail or rod, can be inserted into the hole that is sized so as to receive the implant 125. It is recognized herein that the appropriate trajectory and point of entry (e.g., to minimize pain) of the drilling operation can vary depending on the type of bone and/or the implant that is to be inserted. It is further recognized herein that the appropriate trajectory and point of entry might not be readily accessible in a given operating room, so that a given medical professional might rely on personal knowledge to estimate the appropriate trajectory and point of entry. Further still, even if the appropriate trajectory and point of entry are known, the drilling operation is commonly performed freehand, such that the actual trajectory and point of entry can vary from the appropriate trajectory and point of entry.

Figure 14B:
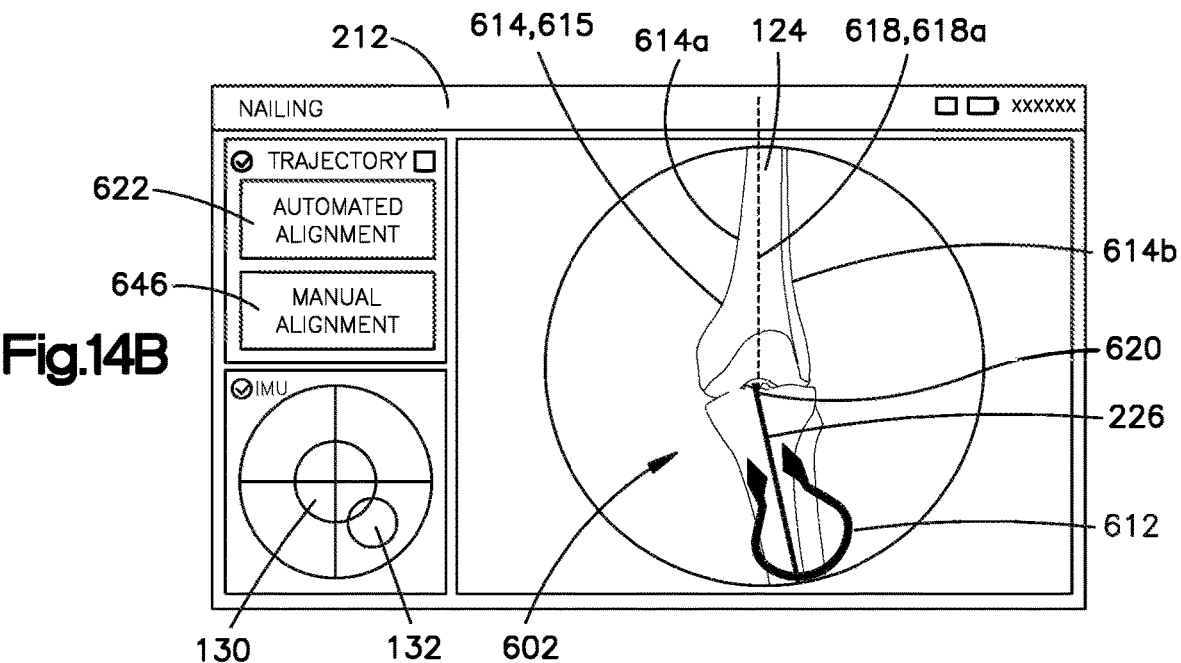
FIG. 14B is an example screen shot of the display of the surgical instrument assembly, wherein the screen shot includes the X-ray image of FIG. 14A with an AP boundary and an AP representation of a trajectory for the specific IM nailing procedure overlayed on the X-ray image.
Figure 17:
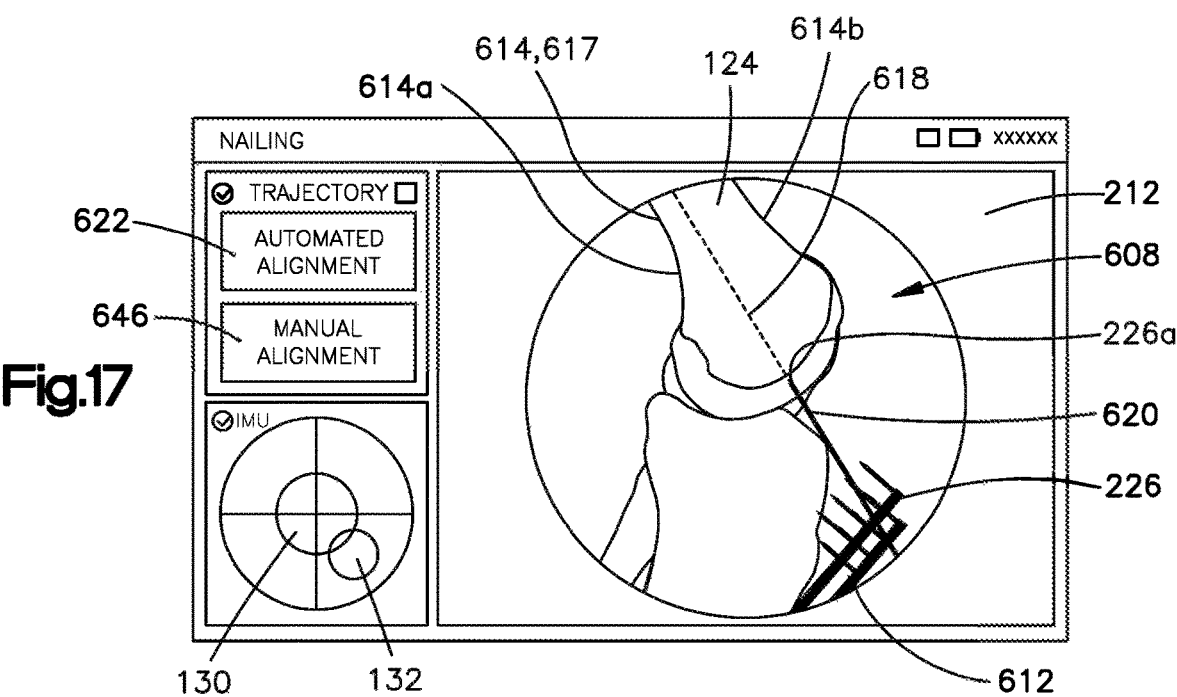
FIG. 17 is an example screen shot of the display of the surgical instrument assembly, wherein the screen shot includes the X-ray image of FIG. 16 but with the position of the cutting instrument adjusted in accordance with the lateral representation of the trajectory.

In an example embodiment, referring to FIGS. 14B and 17, the processor of the surgical instrument assembly 202 can identify or determine a boundary 614, for instance a first or anteroposterior (AP) boundary 615 (FIGS. 14B and 15), or a second or lateral boundary 617 (FIGS. 16 and 17), of the anatomical structure 124. The boundary 614 can define a first outermost edge 614a of the anatomical structure 124 and a second outermost edge 614b of the anatomical structure 124 opposite the first outermost edge 614a. In some examples, the processor can determine the boundary 614 by performing an edge detection process that is described in U.S. Patent Application Publication No. 2007/0274584, disclosure of which is incorporated by reference as if set forth in its entirety herein. It will be understood that other edge detection algorithms may be performed as desired, and the edge detection processes mentioned above are presented for purposes of example. In some cases, the processor can identify the boundary 614 based on a user selection via the user interface 216. For example, the display 212 can display an option, such as a manual alignment option 646. The user, for instance a medical professional, can actuate the manual alignment option 646, for instance by touch or the like. When the manual alignment option 646 is actuated, the user can manually overlay one or more images on the X-ray data, such that the display 212 displays the one or more images on the X-ray data. An example of an image that the user can manually overlay is the boundary 614. By way of example, users can use a stylus, finger, or the like to manually overlay images on the X-ray data. In an example, the user can actuate the manual alignment option 646 to adjust the boundary 614 that is determined by the processor of the surgical instrument assembly 202. For example, the processor can perform an edge detection process to determine the boundary 614, but in some cases, the edge detection process can result in portions of the boundary 614 that are offset from the actual outermost edge of the anatomical structure 124. For instance, the edge detection process might incorrectly identify a fracture in the anatomical structure 124 as a portion of the boundary 614. In the example, the user can, via the user interface 216, adjust the portion of the boundary 614 that is incorrectly identified as representing an outermost edge of the anatomical structure 124. Thus, the surgical instrument assembly 202 can adjust at least a portion, for instance all, of the boundary 614 in response to the user actuating at least one of the options of the user interface 216.

Figure 18:
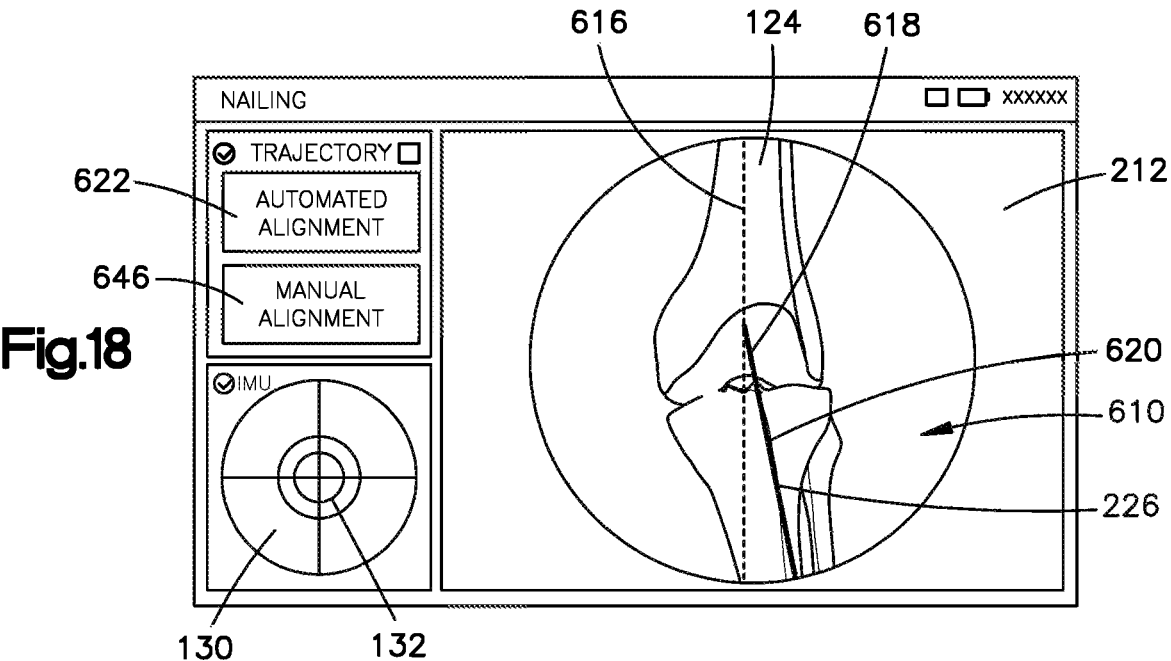
FIG. 18 is another example screen shot of the display of the surgical instrument assembly, wherein the screen shot includes 1) an X-ray image of an anatomical structure; 2) an axis of an anatomical structure overlayed over the X-ray image; and a representation of a trajectory overlayed the X-ray image, wherein the representation of the trajectory is offset at an angle relative to the axis in accordance with an example embodiment.

As shown in FIGS. 14B, 15, 16, and 17, the display 212 can overlay the boundary 614 on the X-ray images of the anatomical structure 124, so as to display the boundaries 614 of the anatomical structure 124. Referring to FIGS. 18 and 20, the processor of the surgical instrument assembly 202 can determine an axis 616 of the anatomical structure 124. The processor of the surgical instrument assembly 202 can determine a representation of a trajectory 618 that defines a point of entry 620 into the anatomical structure. Referring to FIGS. 14B-18 and 20, the display 212 can overlay the representation of the trajectory 618 on the X-ray images of the anatomical structure 124, so as to display the representation of the trajectory 618. The representation of the trajectory 618 can define a line along which a hole can be drilled so as to meet the IM canal of the anatomical structure 124. The representation of the trajectory 618 can be determined based on the axis 616. Further, referring to FIGS. 18 and 20, the display 212 can overlay the axis 616 on the X-ray data of the anatomical structure, so as to display the axis 616 of the anatomical structure 124.

In some examples, the axis 616 can define a centerline along a length of the anatomical structure. Referring to FIGS. 14B-17, the trajectory can be coincident with the axis 616, such that the representation of the trajectory 618 and the axis 616 can overlap each other. For example, the first outermost edge 614a can be spaced from the second outermost edge 614b so as to define a width of the anatomical structure that is substantially perpendicular to the length of the anatomical structure. Thus, the axis 616 can be equidistant from the first outermost edge 614a and the second outermost edge 614b along the length of the anatomical structure 124. In some cases, the processor can identify the axis 616 based on a user selection via the user interface 216. For example, the user, for instance a medical professional, can actuate the manual alignment option 646, for instance by touch or the like. When the manual alignment option 646 is actuated, the user can manually overlay one or more images on the X-ray data, such that the display 212 displays the one or more images on the X-ray data. An example of an image that the user can manually overlay is the axis 616. As shown, the axis 616 is represented as a dashed line, though it will be understood that that the axis 616 can be alternatively represented as desired, for instance by a solid line. By way of example, users can use a stylus, finger, or the like to manually overlay images on the X-ray data. In an example, the user can actuate the manual alignment option 646 to adjust the axis 616 that is determined by the processor of the surgical instrument assembly 202 based on the boundary 614, in particular the first and second outermost edges 614a and 614b. Thus, the surgical instrument assembly 202 can adjust or determine at least a portion, for instance all, of the axis 616 in response to the user actuating at least one of the options of the user interface 216. Further, the surgical instrument assembly 202 can determine the axis 616 of the anatomical structure 124 based on the boundary 614 of the anatomical structure 124 such that, if the boundary 614 of the anatomical structure changes, the axis 616 of the anatomical structure 124 changes in accordance with the changes to the boundary 614. For example, the second outermost edge 614b is adjusted away from first outermost edge 614a, the surgical instrument assembly 202 can move the axis 616 toward the second outermost edge 614b, such that the axis 616 can be displayed farther away from the first outermost edge 614a as compared to where the axis 616 is displayed before the boundary 614 is adjusted.

Without being bound by theory, it is recognized herein that embodiments described herein can lessen the number of X-ray images taken in an operating room, thereby decreasing the time it takes to perform a given operation. In an example, with reference to FIGS. 14A-15 and X-ray image 630a in FIG. 20, the display 212 can display the X-ray image of the anatomical structure 124 from a first or an anteroposterior (AP) view. The surgical instrument assembly can determine the representation of the trajectory 618 that defines the point of entry 620 into the anatomical structure 124. The display 212 can overlay the representation of the trajectory 618 on the X-ray image of the anatomical structure 124, so as to display the representation of the trajectory 618.

In some cases, the processor can determine the representation of the trajectory 618 responsive to a user selection via the user interface 216. For example, the display 212 can display an option, such as an automated alignment option 622. The user, for instance a medical professional, can actuate the automated alignment option 622, for instance by touch or the like. When the automated alignment option 622 is actuated, the processor of the surgical instrument assembly 202 can determine the representation of the trajectory 618 that defines the point of entry 620 into the anatomical structure 124. The surgical instrument assembly can also determine the axis 616 or the boundary 614, or both the axis 616 and the boundary 614, responsive to the automated alignment option 622 being selected or actuated. Further, in response to the automated alignment option 622 being actuated, the display 212 can overlay at least one of, for instance only one of, for instance any combination of, the representation of the trajectory 618, the axis 616, and the boundary 614, on the X-ray images of the anatomical structure 124, so as to display the representation of the trajectory 618, the axis 616, and/or the boundary 614.

In some examples, the surgical instrument assembly 202 can determine the representation of the trajectory 618 based on technique information, for instance technique information stored in the memory 214. Such technique information can include appropriate trajectories for drilling a hole in various bones for placing an IM nail. Based on the technique information, the surgical instrument assembly 202 can determine the representation of the trajectory. By way of example, the technique information may stipulate that the trajectory for a given bone viewed from the AP perspective is 5 degrees lateral of an axis that is measured from a point just below the lesser trochanter. Continuing with the example, the technique information may stipulate that the trajectory for the given bone from the lateral perspective is centered in the greater trochanter and in line with the medullary canal. In an example, the type of bone and nail can be input into the processor via the user interface 216, and the view (e.g., lateral or AP) that corresponds to the X-ray image can be input into the processor via the user interface 216. In response, the processor can retrieve technique information that corresponds to the view of the X-ray image, the type of bone, and the nail. Based on the technique information that is retrieved, the trajectory can be determined. In some cases, the processor first determines the boundary 614, and then determines the axis 616 based on the boundary. The representation of the trajectory 618 can be determined based on the axis 616 and the technique information. For example, the technique information may indicate that that the trajectory is coincident with the axis 616 in a first view, and angularly offset from the axis by a specific angle in a second view that is substantially perpendicular to the first view (see FIG. 19).

Figure 19:
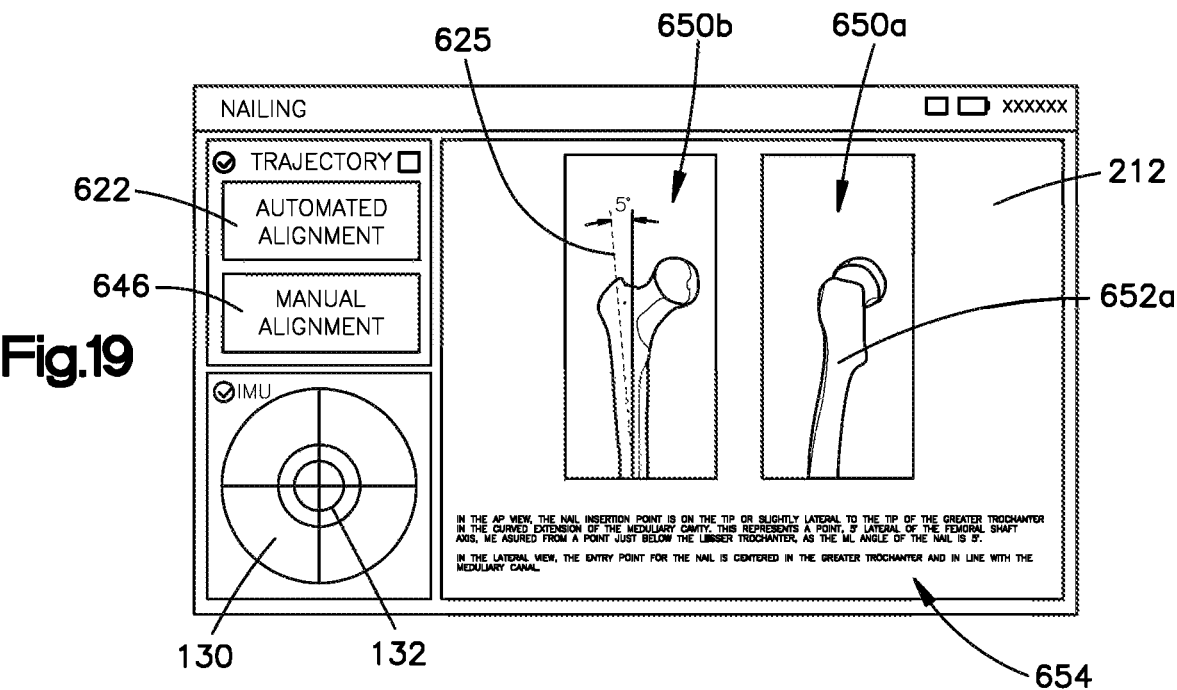
FIG. 19 is another example screenshot of the display of the surgical instrument assembly, showing example technique information associated with an IM nailing procedure.
Figure 20:
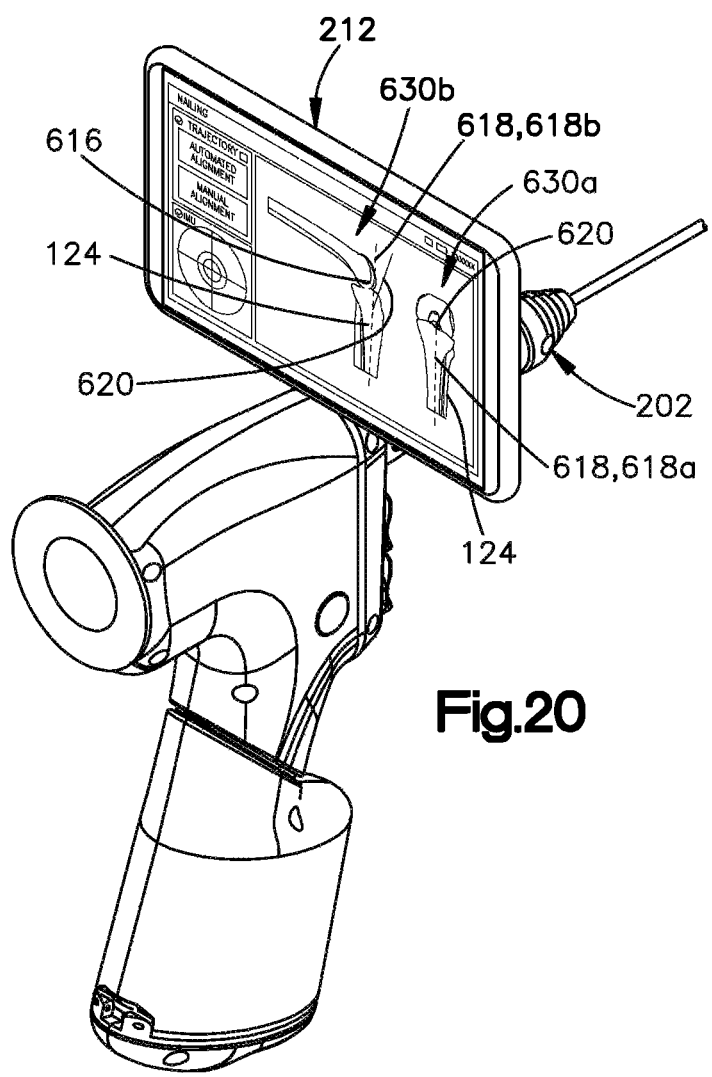
FIG. 20 is a perspective view of the surgical instrument assembly shown in FIG. 7A, showing first and second example X-ray images displayed on the display of the surgical instrument assembly, wherein a first representation of the trajectory is overlayed on the first X-ray image, and second representation of the trajectory is overlayed on the second X-ray image.

Referring to FIG. 19, a given user can retrieve technique information from the surgical instrument assembly actuating a user selection via the user interface 216. For example, the user selection can cause the display 212 to display technique information 650a and 650b. The technique information 650a can include a graphical depiction of an appropriate trajectory 652a from an AP view. The technique information 650b can include a graphical depiction of an appropriate trajectory 652b from a lateral view. The technique information that can be displayed can include instructions 654 in text for placing an IM nail, among other operations. In an example, responsive to a user selection, the user interface 216 can render audible instructions associated with IM nailing operations, among others.

In some cases, a given user, for instance a medical profession, can utilize the technique information rendered by the surgical instrument assembly 202 to manually overlay the representation of the trajectory 618 on a given X-ray image. For example, the user can actuate the manual alignment option 646, for instance by touch or the like. When the manual alignment option 646 is actuated, the user can manually overlay the representation of the trajectory 618, such that the display 212 displays the trajectory 618 on the X-ray data. The representation of the trajectory 618 can define a solid line, a dashed line, or the like. In an example, the user can actuate the manual alignment option 646 to adjust the axis 616 that is determined by the processor of the surgical instrument assembly 202 after the automated alignment option 622 is selected. The surgical instrument assembly 202 can adjust or determine at least a portion, for instance all, of the representation of the trajectory in response to the user actuating at least one of the options of the user interface 216. Thus, the processor of the surgical instrument assembly 202 can adjust the representation of the trajectory so as to define a new representation of the trajectory, and the display 212 can overlay the new representation of the new trajectory on the X-ray image of the anatomical structure, so as to display the new representation of the new trajectory. In an example, the processor can adjust the representation of the trajectory in response to the user actuating at least one of the options of the user interface 216.

Figure 15:
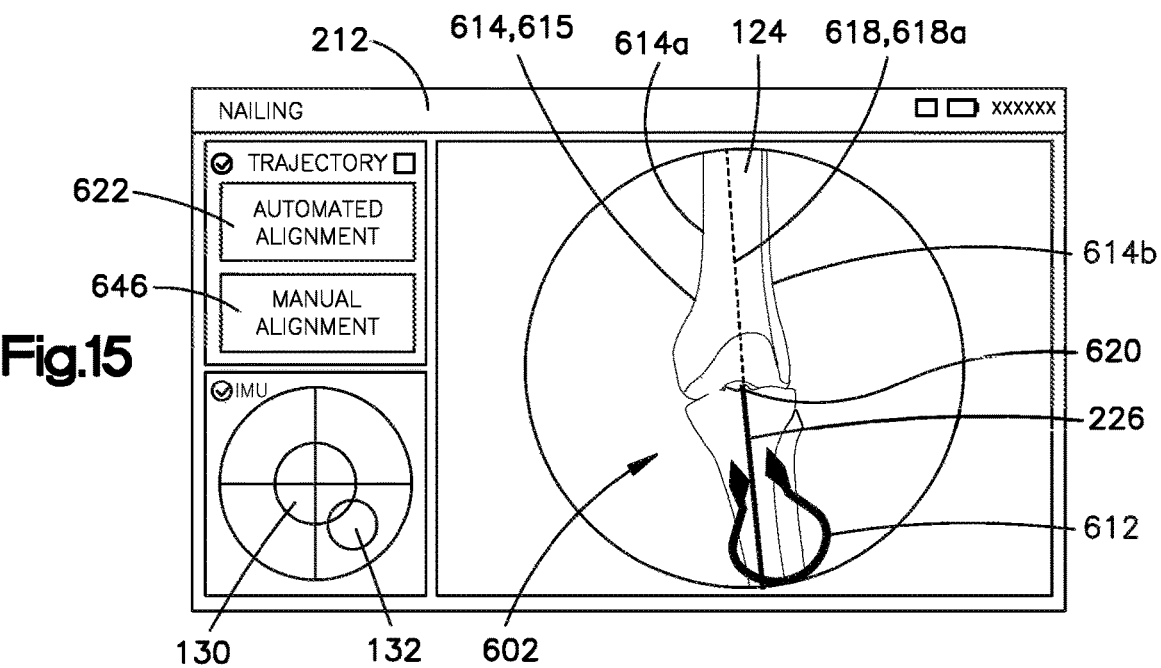
FIG. 15 is an example screen shot of the display of the surgical instrument assembly, wherein the screen shot includes the X-ray image of FIG. 14B but with the position of the cutting instrument adjusted in accordance with the AP representation of the trajectory.
Figure 16:
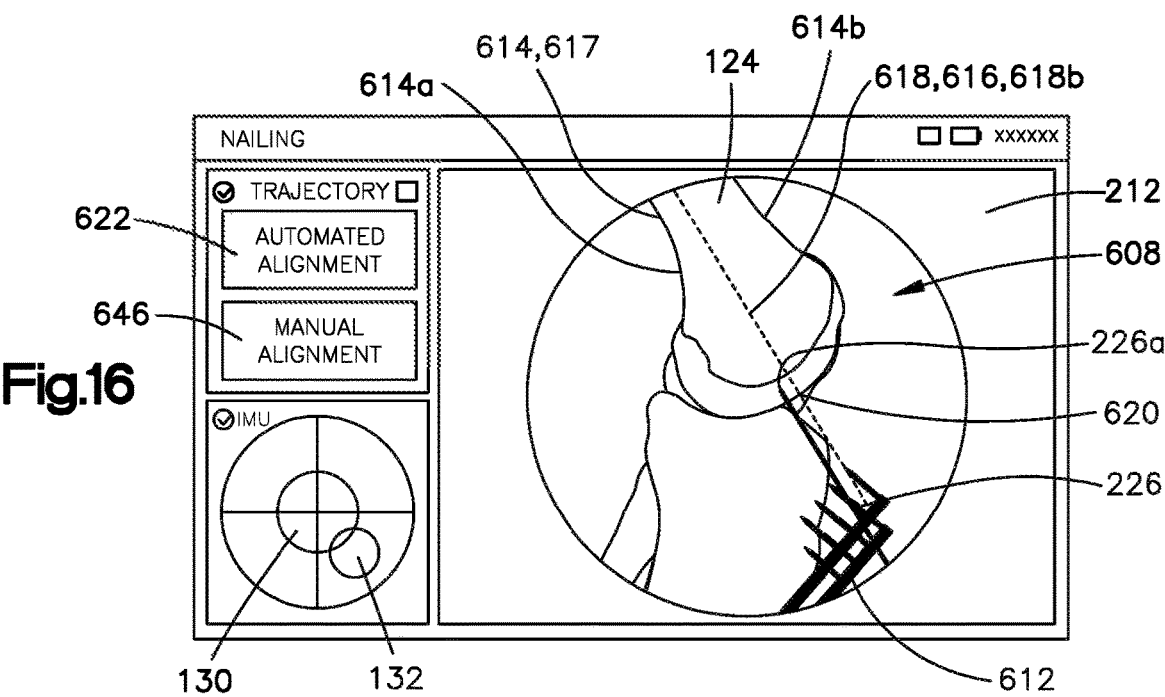
FIG. 16 is an example screen shot of the display of the surgical instrument assembly, showing an X-ray image of the anatomical structure and the cutting instrument shown in FIG. 15, but from a second or lateral view instead of the AP view, wherein the screen shot includes the X-ray image with a lateral boundary and a lateral representation of a trajectory for the specific IM nailing procedure overlayed on the X-ray image.

Referring to FIG. 14B, by viewing the representation of the trajectory 618 and the cutting instrument 226 that is viewable on the X-ray image 602, a user can move the cutting instrument 226 to align with the representation of the trajectory, as shown in the X-ray image 604 of FIG. 15. Alternatively, in an automated scenario, the cutting instrument 226 can be moved automatically so as to align with the representation of the trajectory 618. In an example, when the cutting instrument 226 is aligned with the representation of the trajectory 618, the medical imaging device 104 can be adjusted so as to define a new direction of X-ray travel 128 from the X-ray transmitter 106 to the X-ray receiver 108, so as to generate X-ray images 606 and 608, which is different than the direction of X-ray travel that generated the X-ray images 602 and 604. For example, the medical imaging device 104 can be adjusted so as to generate a second or lateral view that is approximately perpendicular to the first or AP view shown in FIGS. 14B and 15.

Referring to FIGS. 14B, 15, and 20, the representation of the trajectory 618 can be referred to as a first representation 618a of the trajectory from a first perspective, for instance from an AP perspective. In an example, referring to FIGS. 16, 17 and 20, the surgical instrument assembly 202 can determine a second representation 618b of the trajectory that defines the point of entry 620 into the anatomical structure 124. The second representation 618b can be from a second perspective. By way of example, the second perspective can be approximately periocular to the first perspective, such that that first perspective can define an AP view, and the second perspective can define a lateral view. The second representation 618b of the trajectory can be determined and displayed in accordance with any of the embodiments described herein for determining and displaying the representation of the trajectory 618.

Referring to FIGS. 14B-18, the display 212 can display a position of the cutting tip 226a relative to the point of entry 620 of the anatomical structure. By viewing the second representation 618b of the trajectory and the cutting instrument 226 that is viewable on the X-ray images 606 and 608, a user can move the cutting instrument 226, and thus the cutting tip 226a, to align with the second representation 618b of the trajectory. Alternatively, in an automated scenario, the cutting instrument 226 can be moved automatically so as to align with the second representation 618b of the trajectory.

In some cases, when the cutting instrument 226, and thus the cutting tip 226a, is aligned with the first representation of the trajectory 618a and the second representation 618b of the trajectory, the drilling operation can begin, as the cutting instrument 226 is aligned with the appropriate point of entry and trajectory, which can be determined from the technique information described herein. The display 212 can be positioned so as to provide a line of sight to both the tip 226a and the display 212 from a location proximate of the surgical instrument 203, such that a medical professional can view both the X-ray images, and thus the tip 226a, and the anatomical structure 124, so as to center the tip 226a at the point of entry 620.

Referring now to FIG. 18, the display 212 can also be configured to provide a visual indication, for instance the orientation image 629, of an alignment of the cutting instrument 226 with respect to the first representation 618a of the trajectory and the second representation 618b of the trajectory. The visual indication of alignment, for instance the orientation image 629, can be based on the direction of X-ray travel 128, and can further be based on accelerometer information that corresponds to an orientation of the cutting instrument 226. For example, the accelerometer 215 of the surgical instrument assembly 202 can be calibrated with the direction of X-ray travel 128 travel from the X-ray generator 106 to the X-ray receiver 108 of the medical imaging device 104 when the X-ray image 604 from the first perspective is taken, and with the direction of X-ray travel 128 when the X-ray image 608 from the second perspective that is substantially perpendicular to the first perspective is taken.

For example, referring to FIG. 18, the orientation image 629 can include the static region 130 and the movable indicator 132. The movable indicator 132 can be representative of the orientation of the cutting instrument 226. In an example, the cutting instrument 226 is oriented with the first and second representations of the trajectory 618a and 618b when the movable indicator 132 has a predetermined spatial relationship to the static region 130. In an example, a hole is drilled in the anatomical structure 124 while the cutting instrument 226 (e.g., drill bit) is aligned with first and second representations of the trajectory, and the movable indicator 132 has the predetermined spatial relationship to the static region 130. It will be understood that the predetermined spatial relationship can vary as desired. In some cases, for example, the cutting instrument 226 is oriented with the first and second representations of the trajectory when the movable indicator 132 overlies the static region 130. In some cases, the cutting instrument 226 is oriented with the first and second representations of the trajectory when the movable indicator 132 is within a boundary defined by the static region 130.

Figure 9:
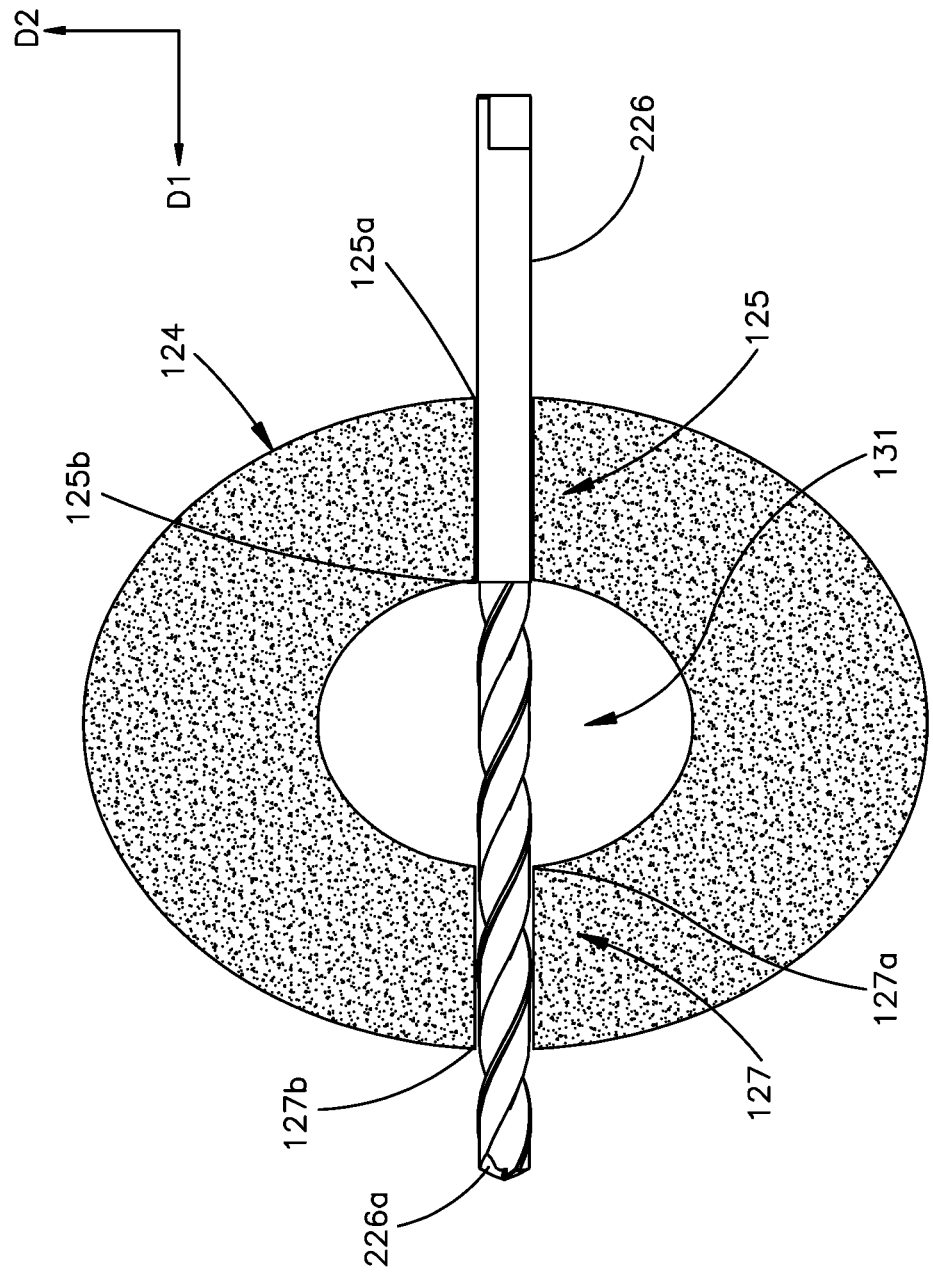
FIG. 9 is a cross section of an example anatomical structure, wherein the cutting instrument has traveled through the anatomical structure along a drilling direction.

Referring now to FIGS. 10A-12, the display 212 can also be configured to provide a visual indication, for instance a depth gauge image 262, of the depth of the cutting tip 226a with respect to one or more portions of the anatomical structure 124. In an example, referring to FIG. 9, the anatomical structure 124 defines a first or near cortex 123 and a second or far cortex 127 opposite the first cortex 123 along the first direction D1 or the direction of X-ray travel 128, which can be in the direction of drilling. The first cortex 123 can define a first or near surface 123a and a second or far surface 123b opposite the first surface 123a along the first direction D1. Similarly, the second cortex 127 can define a first or near surface 127a and a second or far surface 127b opposite the first surface 127a along the first direction D1, which can also be along the direction X-ray travel 128. The anatomical structure 124 can define a hollow portion 131. For example, the hollow portion 131 can be defined between the second surface 123b of the first cortex 123 and the first surface 127b of the second cortex 127. The visual indication of depth, for instance the depth gauge image 262, can change as the cutting instrument 226, in particular the cutting tip 226a, travels into the anatomical structure 124. In particular, the depth gauge image 262 can include data that can change when the cutting instrument tip 226a contacts the respective first and second surfaces of the first cortex 123 and the second cortex 127.

Figure 10A:
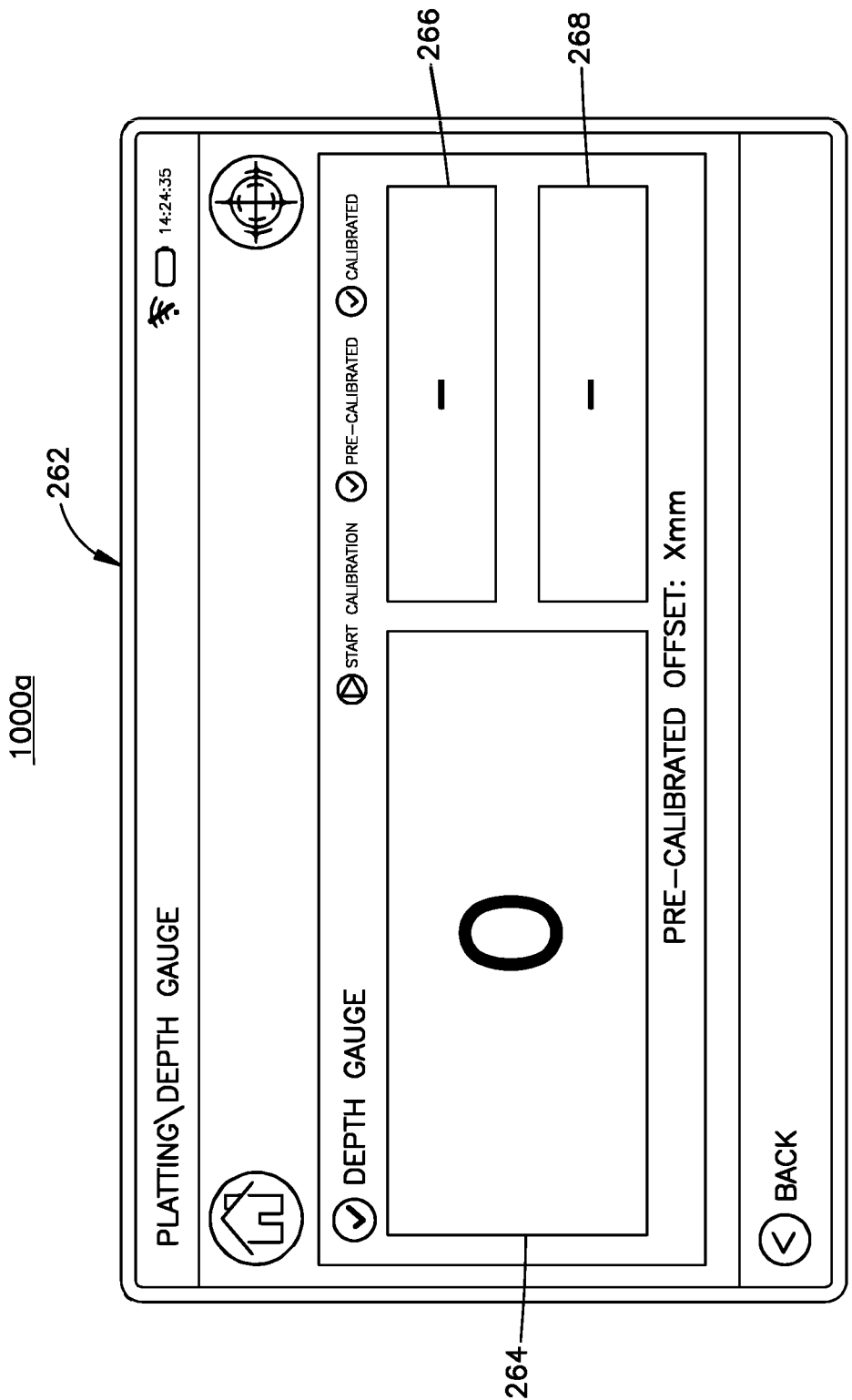
Figure 12:
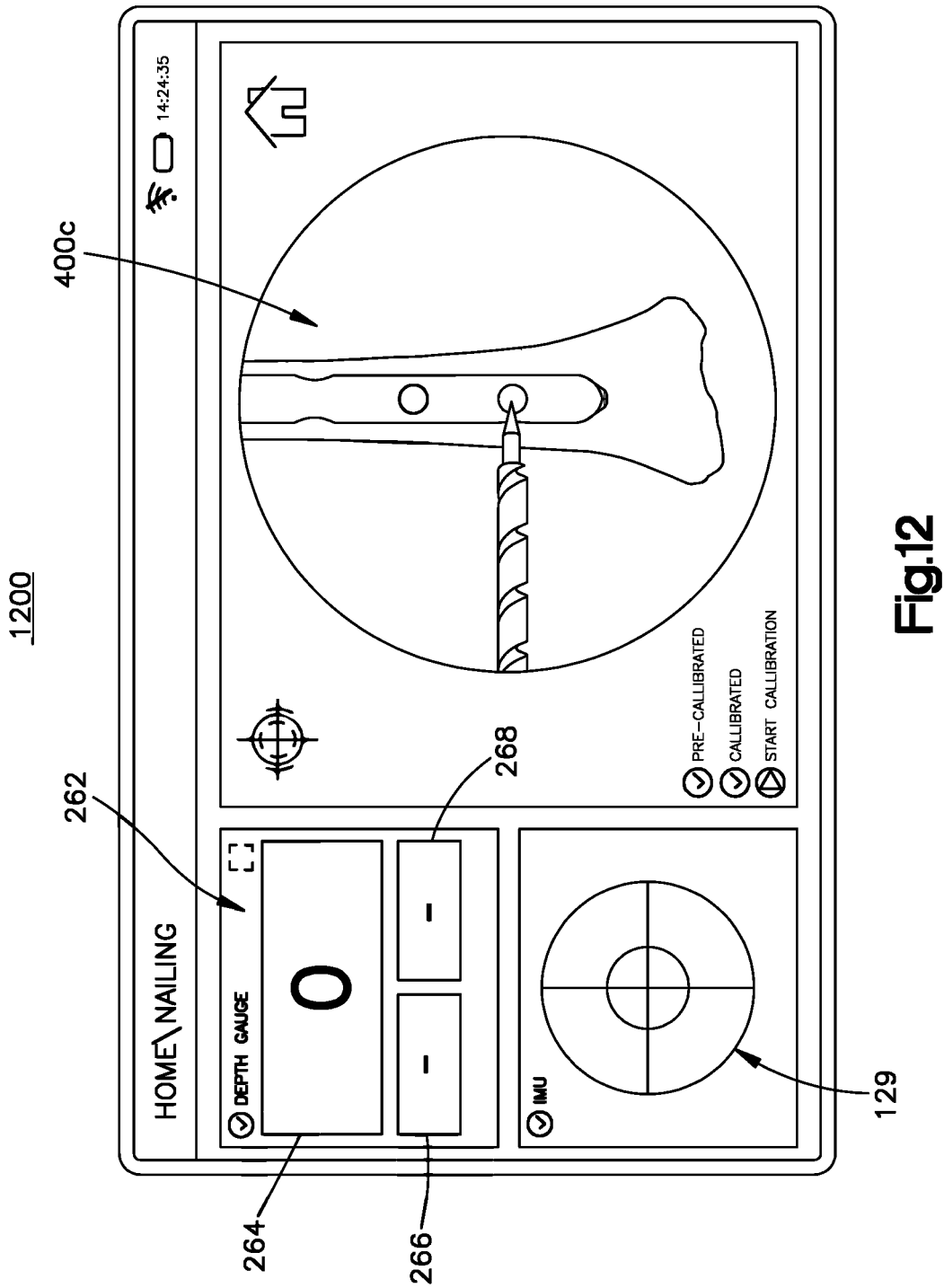
FIG. 12 is another screen shot of the display of the surgical instrument assembly, showing, at the same time: the visual indication of the alignment of the cutting instrument; the visual indication of the depth of the tip of the cutting instrument; and the cutting instrument in an X-ray image of the anatomical structure.
Figure 13:
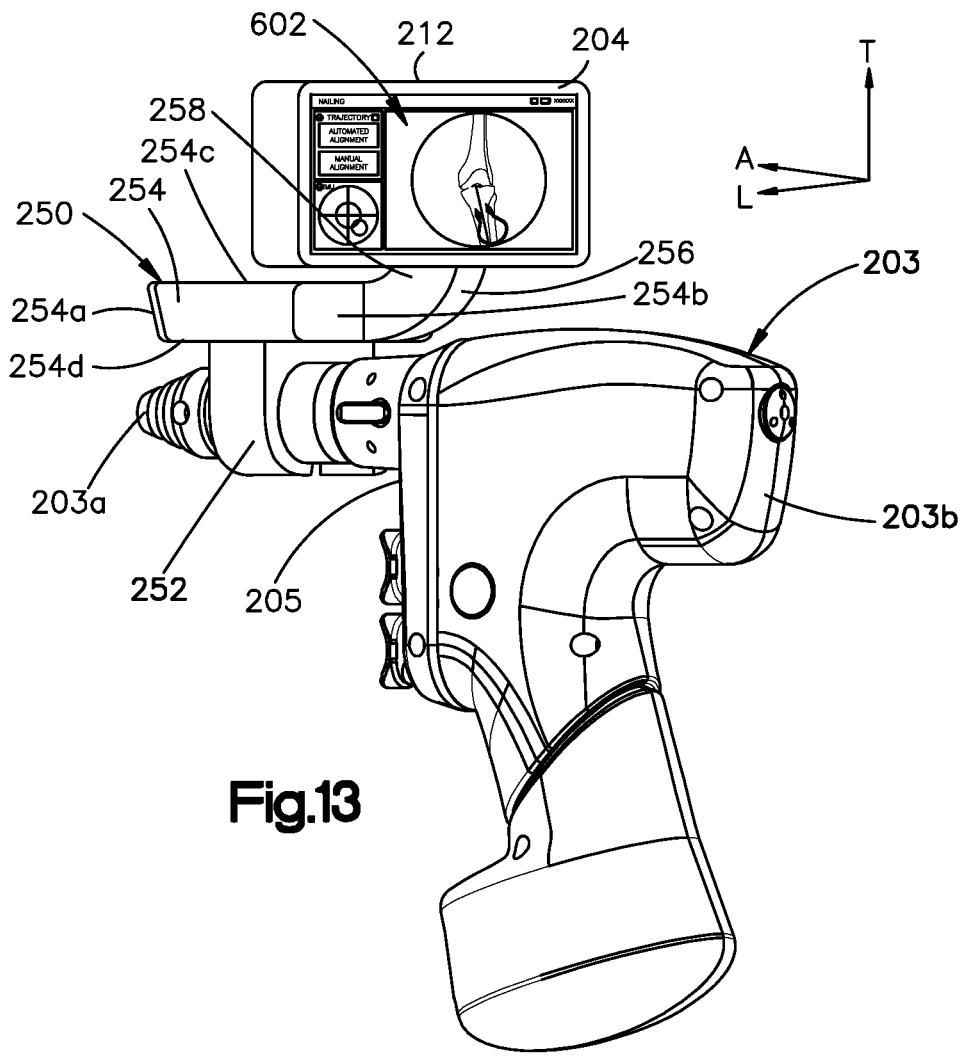
FIG. 13 is a perspective view of the surgical instrument assembly shown in FIG. 7A, showing an example X-ray image displayed on the display of the surgical instrument assembly.

In an example operation, referring first to FIGS. 10A and 12, which depict an example depth gauge screen 1000a and an example split screen 1200, respectively, the depth gauge image 262 is configured to measure a first distance of a reference location relative to a portion of the anatomical structure 124, and the display 212 is configured to indicate a second distance of the cutting tip 226a relative to the portion of the anatomical structure 124. The depth gauge 250 can be configured to measure the first distance as the surgical instrument 203 drills a hole. The display 212 can be configured to indicate the second distance as the surgical instrument drills a hole, so as to indicate the second distance in real-time. The first cortex 123 can define the portion of the anatomical structure 124. In an example, the first cortex 123, in particular the first surface 123a of the first cortex 123, defines the reference location from which the distance from the reference location is measured by the depth gauge 250. In an example, the cutting tip 226a defines the reference location, such that the first distance is equal to the second distance.

In an alternative example, the surgical instrument 203 can include a drill sleeve that defines the reference location from which the distance from the portion of the anatomical structure 124 is measured by the depth gauge 250, such that the first distance is greater than the second distance. The cutting instrument 226 can be placed in the sleeve to protect soft tissue surrounding the bone, among other reasons. During drilling, the depth gauge 250 can determine the distance from a terminal end of the drill sleeve to the first surface 123a of the first cortex 123. The distance from the terminal end of the drill sleeve to the first surface 123a of the first cortex can be greater than the distance from the cutting tip 226a to the first surface 123a of the first cortex 123. Thus, the depth gauge 250 can measure a real-time drill depth distance that is greater than a real-time drill depth distance that the display 212 displays. The difference between the first and second distance can be determined by calibrating the display 212 to account for the distance (which can be referred to as an offset distance) between the cutting tip 226a and the terminal end of the drill sleeve, so that the display 212 provides a total drill depth indication 264 that indicates the distance from the cutting instrument tip to the first surface 123a of the first cortex 123. In an example, a user can enter the offset distance by selecting a calibration option on the user interface 216. In another example, the depth gauge 250 can determine the offset distance during a calibration mode.

Figure 11:
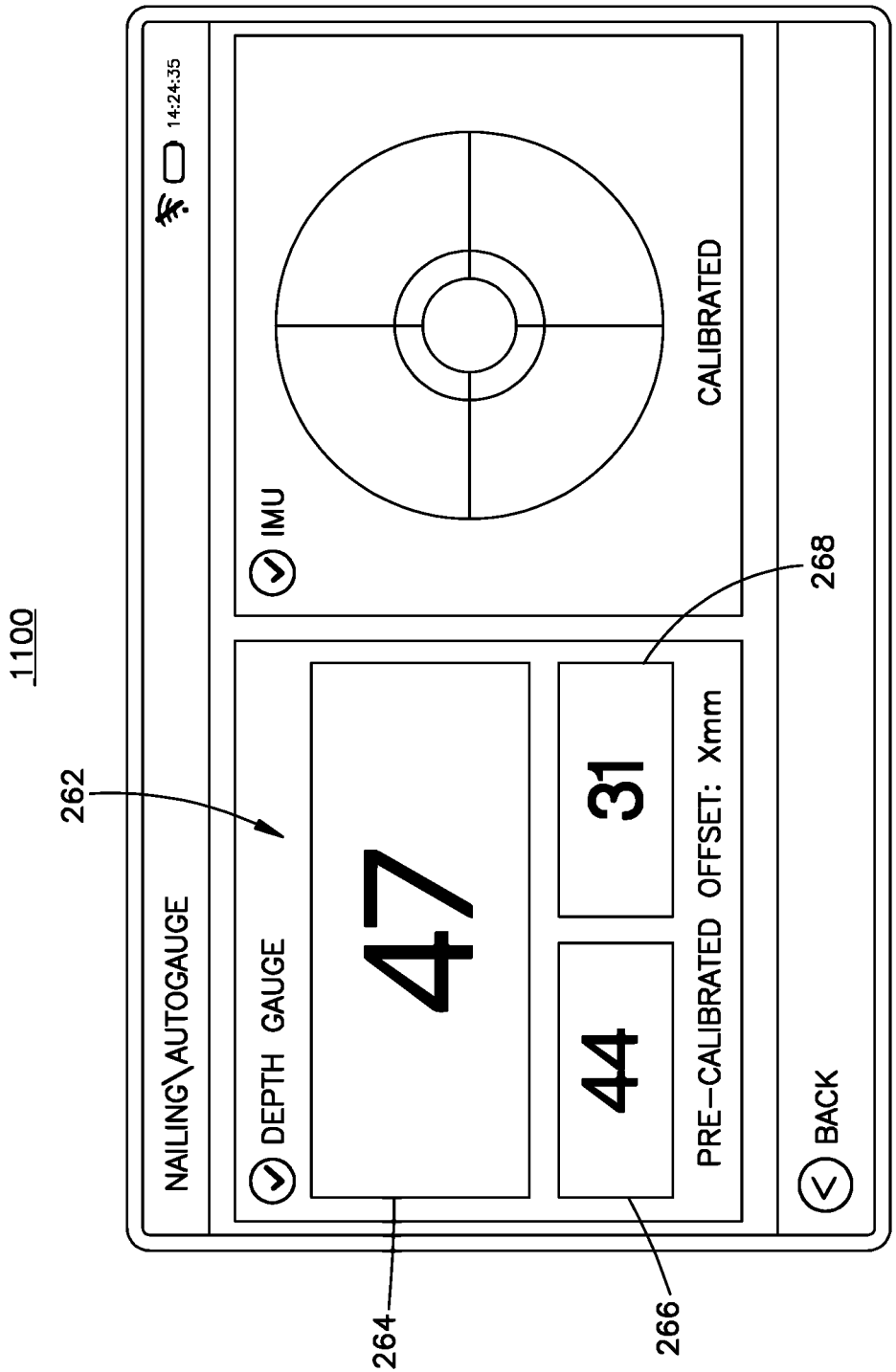
FIG. 11 is an example split screen shot of the display of the surgical instrument assembly, showing, at the same time, the visual indication of the alignment of the cutting instrument and the visual indication of the depth of the tip of the cutting instrument.

The display 212 can display the depth gauge screen 1000a and the example split screen 1000. In the illustrated examples, the total drill depth indication 264 indicates zero (0) when the cutting instrument tip 226a abuts the first surface 123a of the first cortex 123. Alternatively, the depth gauge can be calibrated such that the total drill depth indication 264 can indicate zero (0) when the drill sleeve abuts the first surface 123a of the first cortex 123. The surgical instrument 203 can be configured to drill a hole in the first direction D1 from the first cortex 123 to toward the second cortex 127. Thus, the total drill depth indication 264 can indicate zero (0) before a drilling operation, whereby the cutting instrument tip 226a enters the anatomical structure 124 during the drilling operation. Referring also to FIGS. 10B and 11, which depict an example depth gauge screen 1000b and an example split screen 1100, respectively, as the drilling operation proceeds and the cutting instrument tip 226a travels through the first cortex 123, the total drill depth indication 264 can increase so as to indicate the real-time distance that the cutting instrument tip 226a has traveled with respect to the first surface 123a of the first cortex 123. As shown, the indications of the depth gauge image 262 are rendered in millimeters, though it will be understood that the indications may be rendered in any alternative units.

The depth gauge image 262 can further include a recent cortex exit point indication 266 that indicates the distance from the cutting instrument tip 226a to the far surface of the cortex that was most recently drilled. Thus, the display 212 can be configured to indicate a third distance when the cutting tip 226a exits the first cortex 123, wherein the third distance can represent a width of the first cortex 123 along the first direction D1. As an example, when the cutting instrument tip 226a travels along the first direction D1, which can be the X-ray travel 128, so as to exit the second surface 123b of the first cortex 123, the recent cortex exit point indication 266 indicates the distance from the first surface 123a of the first cortex 123 to the second surface 123b of the first cortex 123. Thus, in an example, at the moment that the cutting instrument tip 226a travels through the second surface 123b of the first cortex 123, the recent cortex exit point indication 266 can indicate the same value as the total drill depth indication 264.

Continuing the drilling operation example, when the cutting instrument tip 226a travels along the first direction D1 so as to exit the second surface 127b of the second cortex 127, the recent cortex exit point indication 266 displays the distance from the first surface 123a of the first cortex 123 to the second surface 127b of the second cortex 127. Thus, the display 212 can be configured to indicate a fourth distance when the cutting tip 226a exits the second cortex 127, and the fourth distance can represent a bone width of the bone along the first direction D1. The display 212 can be configured to indicate the second distance, the third distance, and the fourth distance at the same time. Further, at the moment that the cutting instrument tip 226a travels through the second surface 127b of the second cortex 127, the recent cortex exit point indication 266 can indicate the same value as the total drill depth indication 264. The depth gauge image 262 can further include a previous cortex exit point indication 268 that displays an indication or value associated with the previous, but not most recent, cortex exit point. Thus, continuing with the example, when the cutting instrument tip 226a exits the second surface 127b of the second cortex 127, the previous cortex exit point 268 displays the distance from the first surface 123a of the first cortex 123 to the second surface 123b of the first cortex 123. Thus, the value displayed in the recent cortex exit point indication 266 is moved to the previous cortex exit point indication 268. As the cutting instrument tip 226a travels away from the second surface 127b of the second cortex 127, the total drill depth indication 264 can increase so as to indicate the real-time distance that the cutting instrument tip 226a has traveled with respect to the first surface 123a of the first cortex 123, as exemplified by FIGS. 10B and 11.

Without being bound by theory, a user can view the depth gauge image 262 while the surgical instrument 203 operates, either under user control or autonomously, so as to better perform a drilling operation. For example, the user can view the total drill depth indication 264 while performing a drilling operation, so as to control the surgical instrument based on the total drill depth indication 264. The surgical instrument 203 can be controlled based on the information in the depth gauge image 262 so that the cutting instrument 203 does not enter unwanted portions of the anatomy, such as soft tissue or a far cortex that is not intended to be drilled, either wholly or in part. In some cases, a user can view the depth gauge image 262, in particular the total drill depth indication 264 or the recent cortex exit point indication 266, to match the length of a screw with respective holes that are drilled, instead of having to measure the holes after the drilling operation is performed. In an example, the computing device 204 stores an inventory of available screws, such that a screw is automatically matched to a hole that is drilled, based on the depth of the hole in the anatomical structure 124. In an example, a user can actuate a select screw option on the user interface 216, so that a screw is selected that corresponds to one of the indications on the depth gauge image 262, for instance the recent cortex exit point indication 266 or the total drill depth indication 262.

Thus, in operation, the display 212 can receive and display a plurality of X-ray images in real-time, and the display 212 can display the orientation image 129 and the depth gauge image 262, in particular the total drill depth indication 262, as the surgical instrument 203 is operated. In particular, the depth gauge image 262 can be representative of distances that the cutting instrument 203 as moved. The fluoroscopic images, the orientation images, and the depth gauge images can be displayed by the display 212 at the same time. As the cutting instrument 203 moves along a drilling direction, the distance displayed by the display 212 can change, so as to update the distance in real-time.

Figure 6A:
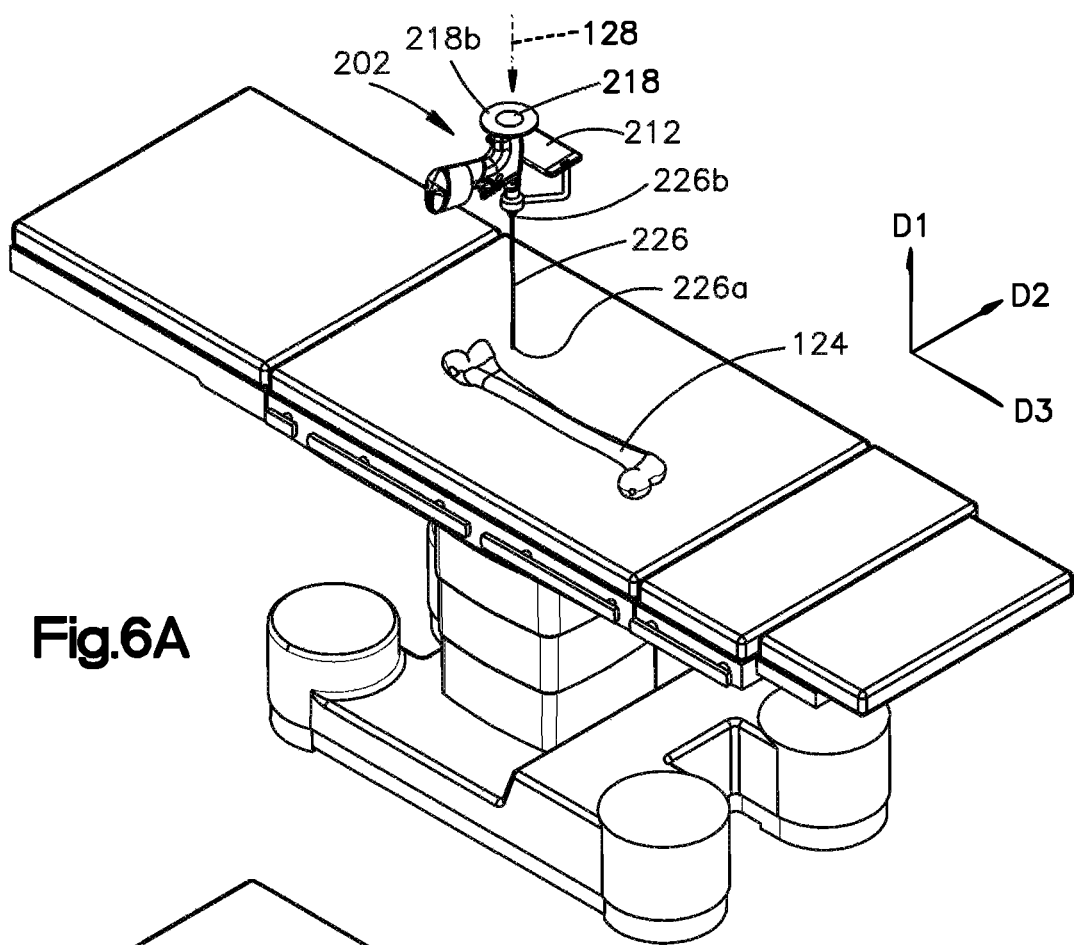
FIG. 6A depicts the example imaging system shown in FIG. 1, showing an example anatomical structure and an example orientation of the surgical instrument assembly.
Figure 6B:
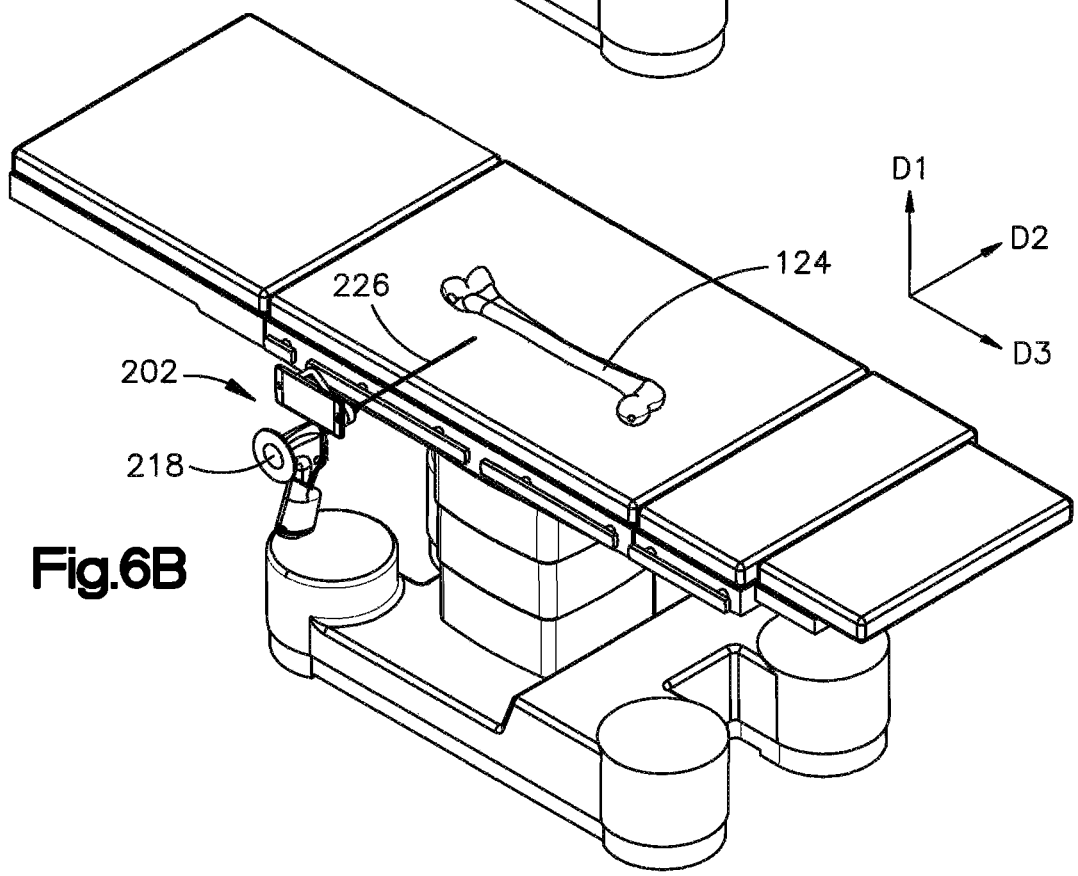
FIG. 6B depicts another example orientation of the surgical instrument assembly in the imaging system shown in FIG. 6A.

In an example, referring to FIG. 6A, the surgical instrument 203 can be operated along the first direction D1 that is parallel to the direction of X-ray travel 128, so as to drill a hole along the first direction D1. During drilling, for example, as the orientation of the cutting instrument 226 moves away from the zero value, the movable indicator 132 can move away from the static region 130. The movable indicator 132 can move relative to the static region 130 at the same time that the orientation of the cutting instrument 226 moves relative to the zero value, such that the movable indicator 132 provides a real-time representation of the orientation of the cutting instrument 226. For example, as the proximal end 226b of the cutting instrument 226 moves along a second direction D2 relative to the cutting tip 226a of the cutting instrument 226, the movable indicator 132 can move along the second direction D2 (e.g., see FIG. 5A). The second direction D2 can be perpendicular to the first direction D1. Similarly, as the proximal end 226b of the cutting instrument 226 moves along a third direction D3 relative to the cutting tip 226a of the cutting instrument 226, the movable indicator 132 can move along the third direction D3 (e.g., see FIG. 5B). The third direction D3 can be perpendicular to both the first and second directions D1 and D2, respectively. Further, it will be understood that as the proximal end 226b of the cutting instrument 226 moves along both the second and third directions relative to the cutting tip 226a of the cutting instrument 226, the movable indicator 132 can move along both the second and third directions D3. Further, the orientation screens 500a-c can include a numerical representation 136 of the orientation of the cutting instrument 226 along the second and third directions D2 and D3.

Referring in particular to FIG. 5C, when the cutting instrument 226 is oriented in accordance with the zero value, the movable indicator 132 can be positioned within a boundary defined by the static region 130. Further, in some cases, when the cutting instrument 226 is precisely aligned with the direction of X-ray travel 128, the numerical representation 136 may indicate that zero values associated with both the second and third directions. By way of an IM nailing example, a medical professional can maintain the orientation image 129 illustrated in FIG. 5C while drilling, so as to drill holes having the appropriate orientation at the target locations 126.

While example embodiments of devices for executing the disclosed techniques are described herein, the underlying concepts can be applied to any computing device, processor, or system capable of communicating and presenting information as described herein. The various techniques described herein can be implemented in connection with hardware or software or, where appropriate, with a combination of both. Thus, the methods and apparatuses described herein can be implemented, or certain aspects or portions thereof, can take the form of program code (i.e., instructions) embodied in tangible non-transitory storage media, such as floppy diskettes, CD-ROMs, hard drives, or any other machine-readable storage medium (computer-readable storage medium), wherein, when the program code is loaded into and executed by a machine, such as a computer, the machine becomes an apparatus for performing the techniques described herein. In the case of program code execution on programmable computers, the computing device will generally include a processor, a storage medium readable by the processor (including volatile and non-volatile memory and/or storage elements), at least one input device, and at least one output device, for instance a display. The display can be configured to display visual information. For instance, the displayed visual information can include fluoroscopic data such as X-ray images, fluoroscopic images, orientation screens, or computer-generated visual representations.

The program(s) can be implemented in assembly or machine language, if desired. The language can be a compiled or interpreted language, and combined with hardware implementations.

The techniques described herein also can be practiced via communications embodied in the form of program code that is transmitted over some transmission medium, such as over electrical wiring or cabling, through fiber optics, or via any other form of transmission. When implemented on a general-purpose processor, the program code combines with the processor to provide a unique apparatus that operates to invoke the functionality described herein. Additionally, any storage techniques used in connection with the techniques described herein can invariably be a combination of hardware and software.

While the techniques described herein can be implemented and have been described in connection with the various embodiments of the various figures, it is to be understood that other similar embodiments can be used or modifications and additions can be made to the described embodiments without deviating therefrom. For example, it should be appreciated that the steps disclosed above can be performed in the order set forth above, or in any other order as desired. Further, one skilled in the art will recognize that the techniques described in the present application may apply to any environment, whether wired or wireless, and may be applied to any number of such devices connected via a communications network and interacting across the network. Therefore, the techniques described herein should not be limited to any single embodiment, but rather should be construed in breadth and scope in accordance with the appended claims.

What is claimed:

1. A surgical instrument assembly comprising:
a processor;
a surgical instrument configured to operate on an anatomical structure;
a display coupled to the processor and attached to the surgical instrument, the display configured to display X-ray data of the anatomical structure, the X-ray data generated by a medical imaging device; and
a memory in communication with the processor, the memory having stored therein instructions that, upon execution of the processor, cause the processor to:
identify an intramedullary nail from a plurality of intramedullary nails so as to determine an intramedullary nail identity, the intramedullary nail defining a plurality of locking holes sized to receive respective locking screws;

receive a first X-ray image from the medical imaging device, the first X-ray image generated by the medical imaging device when the medical imaging device is in a first position such that the first X-ray image includes a portion of the intramedullary nail, the portion of the intramedullary nail including a portion of at least two of the plurality of locking holes; and based on the portion of the at least two locking holes and the intramedullary nail identity, determine a second position of the medical imaging device that is different than the first position, such that, when the medical imaging device is placed in the second position and generates a second X-ray image from the second position, the second X-ray image includes the at least two locking holes shown as respective circles.

2. The surgical instrument assembly as recited in claim 1, wherein the at least two locking holes are spaced apart from each other along a length of the intramedullary nail, and the medical imaging device includes an X-ray transmitter and X-ray receiver so as define a direction of X-ray travel from the X-ray transmitter to the X-ray receiver, the direction of X-ray travel substantially perpendicular to the length of the intramedullary nail when the medical imaging device is in the second position.

3. The surgical instrument assembly as recited in claim 2, the memory having stored therein further instructions that, upon execution of the processor, cause the processor to:
determine adjustment coordinates based on the first and second positions of the medical imaging device, the adjustment coordinates indicating how the direction of X-ray travel is adjusted to arrive at the second position from the first position.

4. The surgical instrument assembly as recited in claim 3, wherein the display is further configured to display the adjustment coordinates.

5. The surgical instrument assembly as recited in claim 4, wherein the display is further configured to display positional coordinates that correspond to an actual position of the X-ray transmitter and the X-ray receiver, the positional coordinates received from the medical imaging device as the actual position of the X-ray transmitter and the X-ray receiver is adjusted, such that the positional coordinates that are displayed change as the X-ray transmitter and the X-ray receiver move.

6. The surgical instrument assembly as recited in claim 1, wherein the display is further configured to indicate the second position responsive to the processor receiving the first X-ray image from the medical imaging device.

7. The surgical instrument assembly as recited in claim 1, the the memory having further stored therein instructions that, upon execution of the processor, further cause the processor to:
determine a third position of the medical imaging device, such that, when the medical imaging device is placed in the third position and generates a third X-ray image from the third position, the third X-ray image includes the third locking hole of the intramedullary nail shown as a circle, the third locking hole different than the at least two locking holes.

8. The surgical instrument assembly as recited in claim 7, wherein the display is further configured to indicate the third position responsive to the processor receiving the first X-ray image from the medical imaging device.

9. The surgical instrument assembly as recited in claim 1, wherein the portion of the at least two locking holes are viewable as respective ellipses on the first X-ray image.

10. The surgical instrument assembly as recited in claim 1, wherein the portion of the intramedullary nail of the of the first x-ray image includes only two locking holes.

11. The surgical instrument assembly as recited in claim 10, wherein the portion of the two locking holes shown in the X-ray image is less than 30% of the two locking holes.

12. A method for determining an orientation for drilling a hole for a locking screw to secure an intramedullary nail to a bone, the method comprising the steps of:
receiving, via a wireless communications channel, a first X-ray image of the bone and a portion of the intramedullary nail within the bone, the first X-ray image generated by a medical imaging device while the medical imaging device is in a first position, the first X-ray image including a first visual perspective of at least two locking holes defined by the intramedullary nail;
identifying the intramedullary nail from a plurality of intramedullary nails so as to determine an intramedullary nail identity that is associated with physical characteristics of the intramedullary nail;
retrieving the physical characteristics of the intramedullary nail based on the intramedullary nail identity; and
based on the first visual perspective of the least two locking holes, and based on the physical characteristics of the intramedullary nail, determining a second position for the medical imaging device,
wherein, when the medical imaging device generates a second X-ray image while the medical imaging device is in the second position, the second X-ray image includes a second visual perspective of the at least two locking holes, the second visual perspective defining circles that correspond to respective perimeters of the at least two locking holes.

13. The method as recited in claim 12, wherein the first visual perspective defines ellipses or lenses that correspond to respective perimeters of the at least two locking holes.

14. The method as recited in claim 12, the method further comprising:
based on the first visual perspective of the at least two locking holes, and based on the physical characteristics of the intramedullary nail, determining a third position for the medical imaging device,
wherein, when the medical imaging device generates a third X-ray image while the medical imaging device is in the third position, the third X-ray image includes a third visual perspective of a third locking hole of the intramedullary nail, the third locking hole not visible in the first X-ray image, the third visual perspective defining a circle that corresponds to a perimeter of the third locking hole.

15. A method of drilling a hole for a locking screw to secure an intramedullary nail to a bone, the method comprising:
identifying the intramedullary nail from a plurality of intramedullary nails so as to determine an intramedullary nail identity that is associated with physical characteristics of the intramedullary nail;
causing a medical imaging device to be in a first position relative to the intramedullary nail;
while the medical imaging device is in the first position, generating a first X-ray image of the bone, the first X-ray image including a portion of the intramedullary nail, the portion of the intramedullary nail including a first visual perspective of a locking hole defined by the intramedullary nail;

based on the first visual perspective of the locking hole, and based on the physical characteristics of the intramedullary nail that are associated with the intramedullary nail identity, determining a second position of the medical imaging device relative to the intramedullary nail;

causing the medical imaging device to be in the second position relative to the intramedullary nail; and while the medical imaging device is in the second position, generating a second X-ray image of the bone, wherein the second X-ray image includes a second visual perspective of the locking hole, and the second visual perspective defines a circle that corresponds to a perimeter of the locking hole.

16. The method as recited in claim 15, the method further comprising:

causing the medical imaging device to be in the second position such that the medical imaging device defines a direction of X-ray travel that is substantially perpendicular to a plane defined by the perimeter of the circle of the second visual perspective of the locking hole.

17. The method as recited in claim 16, further including a motion sensor determining an orientation of the direction of X-ray travel, so as to calibrate an accelerometer with the direction of X-ray travel from an X-ray generator to an X-ray receiver of the medical imaging device.

18. The method as recited in claim 16, the method further comprising:

drilling the hole along the direction of X-ray travel defined by the medical imaging device when the medical imaging device is in the second position.

19. The method as recited in claim 15, wherein the second position is only determined based on the first X-ray image and the physical characteristics of the intramedullary nail, which are based on the intramedullary nail identity.

20. The method as recited in claim 15, the method further comprising:

displaying an indication of the second position, and wherein the medical imaging device is positionally adjustable from the first position to the second position.

* * * * *